United States Patent [19]
Beaulieu et al.

[11] Patent Number: 5,846,941
[45] Date of Patent: *Dec. 8, 1998

[54] ISOSTERIC ANTIHERPES PEPTIDE DERIVATIVES II

[75] Inventors: Pierre Louis Beaulieu, Rosemère; Robert Déziel, Ville Mont-Royal; Montse Llinas Brunet, Pierrefonds; Neil Moss; Raymond Plante, both of Laval, all of Canada

[73] Assignee: Boehringer Ingelheim (Canada) Ltd., Laval, Canada

[*] Notice: The terminal 3 months of this patent has been disclaimed.

[21] Appl. No.: 460,957

[22] Filed: Jun. 5, 1995

Related U.S. Application Data

[63] Continuation-in-part of Ser. No. 324,434, Oct. 17, 1994, Pat. No. 5,574,015, which is a continuation of Ser. No. 25,507, Mar. 3, 1993, abandoned, which is a continuation-in-part of Ser. No. 849,918, Mar. 12, 1992, abandoned.

[30]   Foreign Application Priority Data

Dec. 28, 1994 [CA] Canada ................... 2139169

[51] Int. Cl.$^6$ ..................................................... C07K 7/02
[52] U.S. Cl. ............................. 514/18; 514/17; 514/19; 530/330; 530/331; 530/332; 562/565
[58] Field of Search ............... 514/17–19; 530/330–332; 562/565

[56]   References Cited

U.S. PATENT DOCUMENTS

| | | | |
|---|---|---|---|
| 4,795,740 | 1/1989 | Cohen | 514/14 |
| 4,814,432 | 3/1989 | Friedenger | 530/329 |
| 4,837,304 | 6/1989 | Garsky | 530/328 |
| 4,845,195 | 7/1989 | Colono | 530/330 |
| 5,574,015 | 11/1996 | Beaulieu et al. | 514/18 |

FOREIGN PATENT DOCUMENTS

| | | |
|---|---|---|
| 2033448 | 7/1992 | Canada . |
| 0408973 | 1/1991 | European Pat. Off. . |
| 0411332 | 2/1991 | European Pat. Off. . |
| 0411333 | 2/1991 | European Pat. Off. . |
| 0411334 | 2/1991 | European Pat. Off. . |
| 0412595 | 2/1991 | European Pat. Off. . |
| 0438873 | 7/1991 | European Pat. Off. . |
| 0461546 | 12/1991 | European Pat. Off. . |
| 0560267 | 9/1993 | European Pat. Off. . |
| 0618226 | 10/1994 | European Pat. Off. . |
| 2185024 | 7/1987 | United Kingdom . |

OTHER PUBLICATIONS

Annual Reports in Medicinal Chemistry; 29, "Chapter 15—Antiviral Agents" pp. 145–154; R.E. Boehme et al.

Nature; vol. 32, May 1986; "Specific Inhibition of Herpesvirus Ribonucleotide Reductase by Synthetic Peptides", pp. 439–441, B.M. Dutia et al.

Nature; vol. 32, May 1986, "Specific Inhibition of Herpesvirus Ribonucleotide Reductase by a Nonpeptide Derived from the Carboxy Terminus of Subunit 2", pp. 441–442, E.A. Cohen et al.

The Journal of Biological Chemistry, vol. 262, No. 26, 1987, "Structure–Activity Studies on Synthetic Peptides Inhibiting Herpes Simplex Virus Ribonucleotide Reductase" pp. 12413–12416, P. Gaudreau et al.

Journal of Medicinal Chemistry, vol. 33, 1990, "Synthesis and Inhibitory Potency of Peptides Corresponding to the Subunit 2 C–Terminal Region of Herpes Virus Ribonucleotide Reductase", pp. 723–730, P. Gaudreau et al.

Journal of Medicinal Chemistry, vol. 35, 1992 "Structure-Function Studies Of Peptides Inhibiting the Ribonucleotide Reductase Activity of Herpes Simplex Virus Type I$^1$" pp. 346–350, P. Gaudreau et al.

Bioorganic and Medicinal Chemistry Letters, vol. 2, No. 10, 1992 "Substituted Penta–and Hexapeptides as Potent Inhibitors of Herpes Simplex Virus Type 2 Ribonucleotide reductase" pp. 1207–1212, L.L. Chang et al.

Journal of Medicinal Chemistry, vol. 36, No. 20, 1993, "Inhibition of Herpes Simplex Virus Type 1 Ribonucleotide Reductase by Substituted Tetrapeptide Derivatives" pp. 3005–3009, N. Moss et al.

*Primary Examiner*—Cecilia J. Tsang
*Assistant Examiner*—Bennett Celsa
*Attorney, Agent, or Firm*—R. P. Raymond; M-E. M. Devlin; A. R. Stempel

[57]   ABSTRACT

Disclosed herein are peptidomimetic compounds of the formula A—B—D—CH$_2$CH{CH$_2$C(O)R$^1$}C(O)—NHCH{CR$^2$(R$^3$)COOH}C(O)—E wherein A is a terminal group, for example an optionally substituted phenylalkanoyl, and B is a N-methyl amino acid residue; or A and B together form a saturated or unsaturated alkylaminocarbonyl; D is an amino acid residue; R$^1$ is alkyl, cycloalkyl, a monosubstituted or a disubstituted amino; R$^2$ is hydrogen and R$^3$ is phenylalkyl, or R$^2$ and R$^3$ are joined to form a cycloalkyl; and E is a terminal unit, for example, an alkylamino or a monovalent amino acid radical such as NHCH(alkyl)C(O)OH. The derivatives are useful for treating herpes infections.

16 Claims, 3 Drawing Sheets

ISOSTERIC ANTIHERPES PEPTIDE DERIVATIVES II

This is a continuation-in-part of U.S. application Ser. No. 324,434, filed on Oct. 17, 1994, now U.S. Pat. No. 5,574,015 issued Nov. 12, 1996 which is a continuation of U.S. application 025,507, filed on Mar. 3, 1993 (now abandoned), which is a continuation-in-part of U.S. application 849,918, filed Mar. 12, 1992 (now abandoned).

FIELD OF INVENTION

This invention relates to peptidomimetic compounds having antiviral properties and to means for using the derivatives to treat viral infections. More specifically, the invention relates to compounds exhibiting activity against herpes viruses, to pharmaceutical compositions comprising the compounds, and to methods of using the compounds to inhibit the replication of herpes virus and to treat herpes infections.

BACKGROUND OF THE INVENTION

Herpes viruses inflict a wide range of diseases against humans and animals. For instance; herpes simplex viruses, types 1 and 2 (HSV-1 and HSV-2), are responsible for cold sores and genital lesions, respectively; varicella zoster virus (VZV) causes chicken pox and shingles; and the Epstein-Barr virus (EBV) causes infectious mononucleosis.

Over the past two decades, a class of compounds known as the purine and pyrimidine nucleoside analogs has received the most attention by investigators in the search for new therapeutic agents for treatment of herpes virus infections. As a result, several nucleoside analogs have been developed as antiviral agents. The most successful to date is acyclovir which is the agent of choice for treating genital herpes simplex infections.

Nevertheless, in spite of some significant advances, the need for effective, safe therapeutic agents for treating herpes viral infections continues to exist. For a review of current therapeutic agents in this area, see R. E. Boehme et al., Annual Reports in Medicinal Chemistry, 29, 145 (1994).

The present application discloses a group of peptidomimetic compounds having activity against herpes viruses. The selective action of these compounds against herpes viruses, combined with a wide margin of safety, renders the compounds as desirable agents for combating herpes infections.

The following references disclose peptides or peptidomimetic compounds which have been associated with antiherpes activity:

B. M. Dutia et al., Nature, 321, 439 (1986),
E. A. Cohen et al., Nature, 321, 441 (1986),
J. H. Subak-Sharpe et al., UK patent application 2185024, published Jul. 8, 1987,
P. Gaudreau et al., J. Biol. Chem., 262, 12413 (1987),
E. A. Cohen et al., U.S. Pat. No. 4,795,740, Jan. 3, 1989,
R. Freidinger et al., U.S. Pat. No. 4,814,432, Mar. 21, 1989,
V. M. Garskey et al., U.S. Pat. No. 4,837,304, Jun. 6, 1989,
R. Colonno et al., U.S. Pat. No. 4,845,195, Jul. 4, 1989,
P. Gaudreau et al., J. Med. Chem., 33, 723 (1990),
J. Adams et al., European patent application 408,973, published Jan. 23, 1991,
P. L. Beaulieu et al., European patent application 411,332, published Feb. 6, 1991,
J. Adams et al., European patent application 411,333, published Feb. 6, 1991,
J. Adams et al., European patent application 411,334, published Feb. 6, 1991,
R. L. Tolman et al., European patent application 412, 595, published Feb. 13, 1991,
W. T. Ashton et al., European patent application 438,873, published Jul. 31, 1991,
P. L. Beaulieu et al., European patent application 461,546, published Dec. 18, 1991,
P. Gaudreau et al., J. Med. Chem., 35, 346 (1992), R. Déziel and Y. Guindon, Canadian patent application 2,033,448, published Jul. 1, 1992,
L. L. Chang et al., Bioorganic & Medicinal Chemistry Letters, 2, 1207 (1992),
P. L. Beaulieu et al., European patent application 560 267, published Sep. 15, 1993,
N. Moss et al., J. Med. Chem., 36, 3005 (1993), and
R. Déziel and N. Moss, European patent application 618 226, published Oct. 5, 1994.

The subject peptides of the previous reports can be distinguished from the compounds of the present application by characteristic structural and biological differences.

A noteworthy structural characteristic which distinguishes the present compounds from the usual peptide is that they contain a ketomethylene group in place of an internally located amide group. Hence, the present peptides can be considered to be ketomethylene isosteres.

Abbreviations and symbols used hereinafter are defined in "Details of the Invention" section of this application.

SUMMARY OF THE INVENTION

The compounds of this invention are represented by formula 1

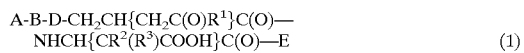

$$A\text{-}B\text{-}D\text{-}CH_2CH\{CH_2C(O)R^1\}C(O)\text{-}NHCH\{CR^2(R^3)COOH\}C(O)\text{-}E \quad (1)$$

wherein

A is phenyl (lower) alkanoyl; phenyl (lower) alkanoyl monosubstituted on the aromatic portion thereof with a lower alkyl, amino, halo, hydroxy or lower alkoxy; lower alkanoyl disubstituted with phenyl or monosubstituted phenyl wherein the monosubstituent is selected from the group consisting of lower alkyl, halo, hydroxy and lower alkoxy; or {phenyl(lower)alkyl}aminocarbonyl; and B is N(CH₃)-CHR⁴C(O) wherein R⁴ is lower alkyl; or A and B taken together form a saturated or unsaturated alkylaminocarbonyl of the formula R⁵-NH-C(O) wherein R⁵ is (2-10C)alkyl, lower cycloalkyl, 1-(lower alkyl)-(lower cycloalkyl), 1-(2-propenyl)-3-butenyl, 1-methyl-1-(2-propenyl)-3-butenyl, 1-ethyl-1-(2-propenyl)-3-butenyl, or a radical of formula Q

wherein $R^{1A}$ is (1-3C)alkyl, $R^{2A}$ is hydrogen or (1-3C)alkyl and $R^3$ is (1-3C)alkyl; D is NH-CHR⁶C(O) wherein R⁶ is lower alkyl or a lower alkyl monosubstituted with carboxy, hydroxy, mercapto or benzyloxy;

R¹ is lower alkyl, lower cycloalkyl, 1-(lower alkyl)-(lower cycloalkyl), or NR⁷R⁸ wherein R⁷ is hydrogen or lower alkyl and R⁸ is lower alkyl, or R⁷ and R8 together with the nitrogen atom to which they are attached form a pyrrolidino, piperidino, morpholino or 4-methylpiperazino;

R² is hydrogen or lower alkyl and R³ is lower alkyl, or R² is hydrogen and R³ is lower alkenyl or phenyl(1-4C)alkyl, or R² and R³ together with the carbon atom to which they are attached form a lower cycloalkyl; and E is NHR⁹ wherein R⁹ is (4-9C)alkyl; lower cycloalkyl; lower cycloalkyl monosubstituted or disubstituted with lower alkyl or (lower alkyl)-(lower cycloalkyl); or E is NHNR¹⁰OR¹¹ wherein R¹⁰ is hydrogen or lower alkyl and R¹¹ is (4-9C)alkyl; or E is NHCH(R¹²)-Z wherein R¹² is (4-9C)alkyl, lower cycloalkyl or (lower cycloalkyl)-(lower alkyl) and Z is CH₂OH, C(O)OH, C(O)NH₂ or C(O)OR¹³ wherein R¹³ is lower alkyl; or a therapeutically acceptable salt thereof;

provided that when A and B together are the radical of formula Q as defined herein, then D-CH₂CH{CH₂C(O)R¹}C(O)-NHCH{CR²(R³)CO-OH}C(O)-E is Tbg-CH₂-(R)-CH(CH₂C(O)Me₃)C(O)-Asp(cyPn)-NH-(R)-CH(Et)CMe₃.

A preferred group of the compounds of this invention is represented by formula 1 wherein A is phenyl(lower)alkanoyl; (4-aminophenyl)-(lower)-alkanoyl; (4-halophenyl)-(lower)alkanoyl, (4-hydroxyphenyl)-(lower)alkanoyl; {4-(lower alkoxy)phenyl}-(lower)alkanoyl; lower alkanoyl disubstituted with phenyl, 4-halophenyl or 4-(lower alkoxy)phenyl; or a phenyl(lower)alkyl-aminocarbonyl; and B is (N-Me)Val, (N-Me)Ile or (N-Me)Tbg; or A and B together form a saturated or unsaturated alkylaminocarbonyl of the formula R⁵-NH-C(O) wherein R⁵ is as defined hereinabove; D is amino acid residue of (S)-2-amino-3-hydroxy-3-methylbutyric acid or (R)-2-amino-3-mercapto-3-methylbutyric acid or an amino acid residue selected from Val, Ile, Tbg and β-EtNva, R¹ is lower alkyl, lower cycloalkyl, 1-(lower alkyl)-(lower cycloalkyl), NMe₂, NEt₂, pyrrolidino or morpholino; R² and R³ are as defined hereinabove; and E is NHR⁹ wherein R⁹ is (4-9C)alkyl; lower cycloalkyl; lower cycloalkyl monosubstituted or disubstituted with lower alkyl; or (lower alkyl)-(lower cycloalkyl); or E is NHNR¹⁰OR¹¹ wherein R¹⁰ is hydrogen, methyl or ethyl and R¹¹ is (4-9C)alkyl; or E is NHCH(R¹²)-Z wherein R¹² is (4-9C)alkyl or (lower cycloalkyl)methyl and Z is as defined hereinabove; or a therapeutically acceptable salt thereof.

A more preferred group of the compounds is represented by formula 1 wherein A is phenylacetyl, phenylpropionyl, (4-amino-phenyl)propionyl, (4-fluorophenyl)propionyl, (4-hydroxyphenyl)propionyl, (4-methoxyphenyl)propionyl, 2-(phenylmethyl)-3-phenylpropionyl, 2-{(4-fluorophenyl)methyl}-3-(4-fluorophenyl)propionyl, 2-{(4-methoxyphenyl)methyl}-3-(4-methoxyphenyl)-propionyl or benzylaminocarbonyl; B is (N-Me)-Val or (N-Me)Ile; D is Val, Ile or Tbg; R¹ is 1-methylethyl, 1,1-dimethylethyl, 1-methylpropyl, 1,1-dimethylpropyl, 2,2-dimethylpropyl, cyclobutyl, cyclopentyl, cyclohexyl, 1-methylcyclopentyl, NMe₂, NEt₂, pyrrolidino or morpholino; R² is hydrogen and R³ is methyl, ethyl, 1-methylethyl, 1,1-dimethylethyl, propyl, 2-propenyl or benzyl, and the carbon atom bearing R² and R³ has the (R)-configuration, or R² and R³ each independently is methyl or ethyl, or R² and R³ together with the carbon atom to which they are attached form a cyclobutyl, cyclopentyl or cyclohexyl; and E is NHR⁹ wherein R⁹ is 2-methylpropyl, 2,2-dimethylpropyl, 1(R),2,2-trimethylpropyl, 1,1,2,2-tetramethylpropyl, 1(R)-ethyl-2,2-dimethylpropyl, 2-(R,S)-methylbutyl, 2,2-dimethylbutyl, 3,3-dimethylbutyl, 1(R),2,2-trimethylbutyl, 1(R),3,3-trimethylbutyl, 2-ethylbutyl, 2,2-diethylbutyl, 2-ethyl-1(R)-methylbutyl, 2-ethyl-2-methylbutyl, 1(R)-ethyl-3,3-dimethylbutyl, 2,2-dimethylpentyl, cis- or trans-2-methylcyclohexyl, 2,2-dimethylcyclohexyl or cyclohexylmethyl; or E is NHNR¹⁰OR¹¹ wherein R¹⁰ is hydrogen, methyl or ethyl and R¹¹ is 1,1-dimethylethyl; or E is NHCH(R¹²)-Z wherein the carbon atom bearing R¹² has the (S)-configuration, R¹² is 1,1-dimethylethyl, 1-methylpropyl, 2-methylpropyl, 2,2-dimethylpropyl or cyclohexylmethyl and Z is CH₂OH, C(O)OH, C(O)NH₂ or C(O)OR¹³ wherein R¹³ is methyl, ethyl or propyl; or a therapeutically acceptable salt thereof.

Another more preferred group of the compounds is represented by formula 1 wherein A and B together form a saturated or unsaturated alkylaminocarbonyl selected from the group of butylaminocarbonyl, 1-methylethylamino-carbonyl, 1-methylpropylaminocarbonyl, 1-ethylpropylaminocarbonyl, 1,1-dimethylbutylaminocarbonyl, 1-ethylbutylaminocarbonyl, 1-propylbutylaminocarbonyl, 1-ethylpentylaminocarbonyl, 1-butylpentylaminocarbonyl, 2-ethylbutylaminocarbonyl, 2-ethylpentylaminocarbonyl, 1-methyl-1-propylbutylaminocarbonyl, 1-ethyl-1-propylbutylaminocarbonyl, 1,1-dipropylbutyl-aminocarbonyl, (1-propylcyclopentyl)aminocarbonyl, (1-propylcyclohexyl)aminocarbonyl,1-(2-propenyl)-3-butenylaminocarbonyl, 1-methyl-1-(2-propenyl)-3-butenylaminocarbonyl and 1-ethyl-1-(2-propenyl)-3-butenylaminocarbonyl, and D, R¹, R², R³ and E are as defined in the last instance; or a therapeutically acceptable salt thereof.

Still another more preferred group of the compounds of this invention is represented by formula 1 wherein A and B together form a saturated alkyl aminocarbonyl of the formula Q'

(Q')

wherein R¹ᴬ and R³ᴬ are both methyl or both ethyl, and R²ᴬ is hydrogen, methyl or ethyl, and the remaining portion of formula 1 (i.e. D-CH₂CH{CH₂C(O)R¹}C(O)-NHCH{CR²(R³)COOH}C(O)-E) is Tbg-CH₂-(R)-CH(CH₂C(O)Me₃)C(O)-Asp(cyPn)-NH-(R)-CH(Et)CMe₃; or a therapeutically acceptable salt thereof.

A most preferred group of the compounds is represented by formula 1 wherein A is phenylpropionyl, 2-(phenylmethyl)-3-phenylpropionyl or benzylaminocarbonyl; B is (N-Me)Val; D is Tbg; R¹ is 1-methylethyl, 1,1-dimethylethyl, 1-methylpropyl, 1,1-dimethylpropyl, 2,2-dimethylpropyl, cyclobutyl, cyclopentyl, cyclohexyl or 1-methylcyclopentyl; R² is hydrogen and R³ is methyl, ethyl, 1-methylethyl, propyl or benzyl, and the carbon atom bearing R² and R³ has the (R)-configuration, or R² and R³ each independently is methyl or ethyl, or R² and R³ together with the carbon atom to which they are attached form a cyclobutyl, cyclopentyl or cyclohexyl; and E is NHR⁹ wherein R⁹ is 2,2-dimethylpropyl, 1(R),2,2-trimethylpropyl, 1(R)-ethyl-2,2-dimethylpropyl, 2,2-dimethylbutyl or 1(R)-ethyl-3,3-dimethylbutyl or E is NHCH(R¹²)-Z wherein the carbon atom bearing R¹² has the (S)-configuration, R¹² is 2,2-dimethylpropyl and Z is CH₂OH, C(O)OH, C(O)NH₂ or C(O)OR¹³ wherein R¹³ is methyl, ethyl or propyl; or a therapeutically acceptable salt thereof.

Another most preferred group of the compounds is represented by formula 1 wherein A and B together form a saturated or unsaturated alkylaminocarbonyl selected from the group of 1-ethylpropylaminocarbonyl, 1-ethylbutylaminocarbonyl, 1-propylbutylaminocarbonyl, 2-ethylpentylaminocarbonyl, 1-methyl-1-propylbutylaminocarbonyl, 1-ethyl-1-propylaminocarbonyl, 1,1-dipropylbutylaminocarbonyl, (1-propylcyclopentyl)-aminocarbonyl, 1-(2-propenyl)-3-butenylaminocarbonyl and 1-ethyl-1-(2-propenyl)-3-butenylaminocarbonyl; and D, $R^1$, $R^2$, $R^3$ and E are as defined in the last instance; or a therapeutically acceptable salt thereof.

Still another most preferred group of the compounds of this invention is represented by formula 1 wherein A and B together form a saturated alkyl aminocarbonyl of the formula Q'

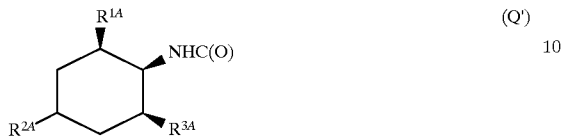

wherein $R^{1A}$ and $R^{3A}$ are both methyl and $R^{2A}$ is hydrogen or a cis-methyl relative to $R^{1A}$ and $R^{3A}$, and the remaining portion of formula 1 is Tbg-CH$_2$-(R)-CH(CH$_2$C(O)Me$_3$)C(O)-Asp(cyPn)-NH-(R)-CH(Et)CMe$_3$; or a therapeutically acceptable salt thereof.

Included within the scope of this invention is a pharmaceutical composition comprising an anti-herpes virally effective amount of a compound of formula 1, or a therapeutically acceptable salt thereof, and a pharmaceutically acceptable carrier.

Also included within the scope of this invention is a cosmetic composition comprising a compound of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective amount of the compound of formula 1, or a therapeutically acceptable salt thereof.

Another important aspect involves a method of inhibiting the replication of herpes virus by contacting the virus with a herpes viral ribonucleotide reductase inhibiting amount of the compound of formula 1, or a therapeutically acceptable salt thereof.

Still another aspect involves a method of treating a herpes viral infection in a mammal by administering thereto an antiheroes virally effective amount of a combination of the compound of formula 1, or a therapeutically acceptable salt thereof, and an antiviral nucleoside analog. A pharmaceutical composition comprising the combination is also within the scope of this invention.

Processes for preparing the compounds of formula 1 are described hereinafter.

DETAILS OF THE INVENTION

GENERAL

Figure 1:
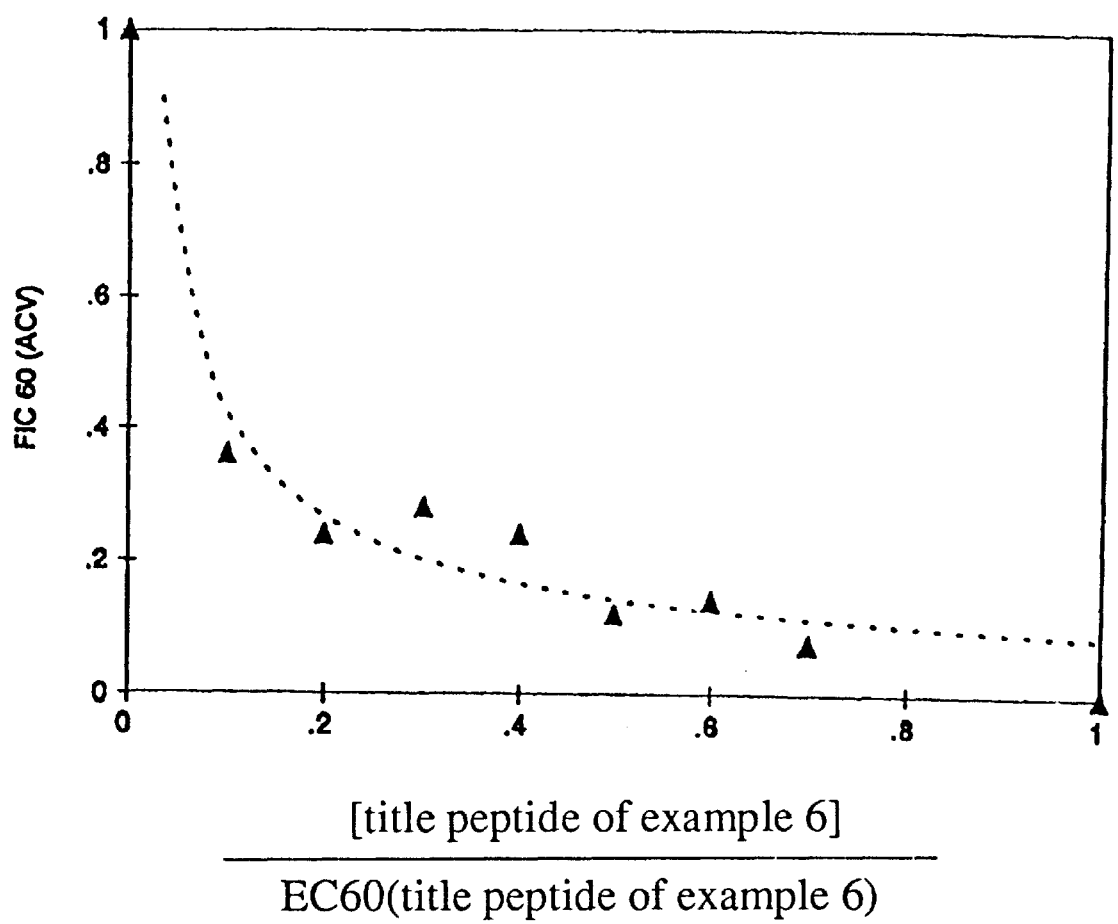
FIGS. 1, 2 and 3 are isobolograms showing the synergistic inhibition of herpes simplex virus replication by combinations of acyclovir and peptidomimetic compounds of formula 1. The respective figures graphically illustrate results obtained in accordance with the isobole method, described in examples 18 and 19, with acyclovir and PhCH$_2$CH$_2$C(O)-(N-Me)Val-Tbg-CH$_2$-(R)-CH(CH$_2$C(O)CMe$_3$)$_3$C(O)-Asp(cyPn)-γMeLeucinol of example 6, against HSV-2 replication (FIG. 1), and with acyclovir and {{(1α,2α,6α)-2,6-dimethyl-1-cyclohexanamino}carbonyl}-Tbg-(R)-CH(CH$_2$C(O)-CMe$_3$)C(O)-Asp(cyPn)-NH-(R)-CH(Et)CMe$_3$ of example 15 against HSV-2 (FIG. 2) and against HSV-1 (FIG. 3). The concentration of the compound was varied and the inhibition of virus replication was assessed. The FIC60 (acyclovir) is the ratio of the concentration of acyclovir required to inhibit virus replication by 60% in the presence of a given concentration of the compound. (FIC stands for fractional inhibitory concentration.) The x axis is the ratio of a given concentration of the compound to the concentration of the compound producing 60% inhibition of virus replication in the absence of acyclovir.

Alternatively, formula 1 can be illustrated as:

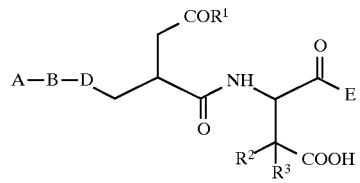

The term "residue" with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Val, Ile, Asp, and Leu represent the residues of L-valine, L-isoleucine, L-aspartic acid and L-leucine, respectively.

The asymmetric carbon atoms residing in the principal linear axis (i.e. the backbone) of the peptides of formula 1, exclusive of the terminal groups A and Z (of E) but including the carbon atom bearing "$R^{12}$" when E is NHCH($R^{12}$)-Z as defined herein, have an (S)-configuration. Exceptions occur, however, for the carbon atom bearing the CH$_2$C(O)R$^1$ side chain wherein $R^1$ is lower alkyl, lower cycloalkyl or 1-(lower alkyl)-(lower cycloalkyl), and for the carbon atom bearing a 2-mecaptoalkyl side chain in the instance when $R^6$ of D is the last mentioned side chain. For the latter two exceptions, the carbon atoms have the (R)-configuration.

Asymmetric carbon atoms residing in the side chain of an amino acid or derived amino acid residue, in the terminal group A, and in the terminal group E when E represents NHR$^9$ as defined herein, may have the (S) or (R)-configuration.

The symbols "Me", "Et", "Pr" and "Bu" represent the alkyl radicals methyl, ethyl, propyl and butyl, respectively.

The symbols "MeEt$_2$C" and "EtPr$_2$C", for example, represent the radicals 1-ethyl-1-methylpropyl and 1-ethyl-1-propylbutyl, respectively.

The symbol "Tbg" represents the amino acid residue of (S)-2-amino-3,3-dimethylbutanoic acid. The symbol "Cpg" represents the amino acid residue of (S)-α-aminocyclopentaneacetic acid. The symbol "γMeLeu" represents the amino acid residue of (S)-2-amino-4,4-dimethylpentanoic acid. The symbol "γMeLeucinol" represents (S)-2-amino-4,4-dimethylpentanol with one hydrogen removed from the α-amino group. The symbol "β-EtNva" represents the amino acid residue of (S)-2-amino-3-ethylpentanoic acid.

Other symbols used herein are: (N-Me)Val for the residue of (S)-3-methyl-2-(methylamino)-butanoic acid; (N-Me)Ile for the residue of (S)-3-methyl-2-(methylamino)pentanoic acid; (N-Me)Tbg for the residue of (S)-2-(methylamino)-3,3-dimethyl butanoic acid; Asp(cyBu) for the residue of (S)-α-amino-1-carboxycyclobutaneacetic acid; Asp(cyPn) for the residue of (S)-α-amino-1-carboxycyclopentaneacetic acid; Asp{(R)-Me} for the residue of 3-(R)-methyl-L- aspartic acid (i.e. {S-(R*,S*)}-2-amino-3-methylbutanedioic acid), Asp{(R)-Pr} for the residue of 3-(R)-propyl-L-aspartic acid (i.e. {S-(R*,S*)}-2-amino-3-propylbutanedioic acid), and Asp{(R)-allyl} for the residue of 3-(R)-allyl-L-aspartic acid (i.e. {S-(R*,S*)}-2-amino-3-(2-propenyl)butanedioic acid).

The term "halo" as used herein means a halo radical selected from bromo, chloro, fluoro or iodo.

The term "(1-3C)alkyl" as used herein means an alkyl radical selected from the group consisting of methyl, ethyl, propyl or isopropyl.

The term "(2-10C)alkyl" as used herein means straight and branched chain alkyl radicals containing from two to ten carbon atoms and includes ethyl, butyl, 1-methylpropyl, 1-ethylpropyl, 1-propylbutyl, 2-propylpentyl and the like.

The term "(4-9C)alkyl" as used herein means straight and branched chain alkyl radicals containing from four to nine carbon atoms and includes, for example, 1-methylpropyl, 2-methylpropyl, 2,2-dimethylpropyl, 1,2,2-trimethylpropyl, 3,3-dimethylbutyl, 1-ethyl-2,2-dimethylbutyl and 4,4-dimethylpentyl.

The term "lower alkyl" as used herein, either alone or in combination with another radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "1-(lower alkyl)-(lower cycloalkyl)" as used herein means a lower cycloalkyl radical bearing a lower alkyl substituent at position 1; for example, 1-ethylcyclopropyl, 1-propylcyclopentyl and 1-propylcyclohexyl.

The term "lower cycloalkyl" as used herein, either alone or in combination with another radical, means saturated cyclic hydrocarbon radicals containing from three to six carbon atoms and includes cyclopropyl, cyclobutyl, cyclopentyl and cyclohexyl.

The term "lower alkenyl" as used herein means straight chain alkenyl radicals containing two to six carbon atoms and branched chain alkenyl radicals containing three to six carbon atoms and includes vinyl, 1-propenyl, 2-propenyl, 1-methylethenyl, 2-methyl-1-propenyl, 2-methyl-2-propenyl and 2-butenyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "phenyl-(1-4C)alkyl" as used herein means phenylalkyl radicals wherein the alkyl portion thereof is a straight or branched chain alkyl containing from one to four carbon atoms and includes benzyl, 2-phenylethyl, 3-phenylpropyl, 2-methyl-2-phenylethyl {PhCH(CH$_3$)CH$_2$}, 1-ethyl-2-phenylethyl {PhCH$_2$CH(C$_2$H$_5$)} and the like.

The term "lower alkanoyl" as used herein, either alone or in combination with another radical, means a 1-oxoalkyl radical wherein the 1-oxoalkyl portion thereof is a straight or branched chain 1-oxoalkyl containing from two to six carbon atoms; for example, acetyl, propionyl (1-oxopropyl) and 1-oxo-5-methylhexyl.

The term "pharmaceutically acceptable carrier" as used herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "effective amount" means a predetermined antiviral amount of the antiviral agent, i.e. an amount of the agent sufficient to be effective against the herpes virus in vivo.

Process

The compounds of formula 1 can be prepared by processes which incorporate therein methods commonly used in peptide synthesis such as the classical solution coupling of amino acid residues and/or peptide fragments. Such methods are described, for example, by E. Schröder and K. Lübke, cited above, in the textbook series, "The Peptides: Analysis, Synthesis, Biology", E. Gross et al., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptidomimetic compounds is the protection of the reactive side chain groups of the various amino acid residues or derived amino acid residues (or, if required, other fragments of the compound) with suitable protective groups which will prevent a chemical reaction from occurring at that site until the protective group is ultimately removed. Also common is the protection of an α-amino group on an amino acid or a fragment while that entity reacts at the carboxy group, followed by the selective removal of the α-amino protective group to allow subsequent reaction to take place at that location. Another common feature is the initial protection of the C-terminal carboxyl of the amino acid residue or fragment, if present, which is to become the C-terminal function of the compound, with a suitable protective group which will prevent a chemical reaction from occurring at that site until the protective group is removed after the desired sequence of the compound has been assembled.

In general, therefore, a compound of formula 1 can be prepared by the stepwise coupling, in the order of the sequence of the compound, of the appropriate amino acid or derived amino acid residues, and non-peptidic fragments of the compound (such as the key intermediates), which if required are suitably protected, and eliminating all protecting groups, if present, at the completion of the stepwise coupling to obtain the compound of formula 1. More specific processes are illustrated in the examples hereinafter.

A key intermediate for the compounds of formula 1 is the intermediate of formula

wherein W is an α-aminoprotective group, e.g. tert-butyloxycarbonyl (Boc), benzyloxycarbonyl (Z) or fluoren-9-ylmethoxycarbonyl (Fmoc), and D and R$^1$ are as defined herein.

An exception to the general methods to prepare the compounds of this invention, however, is a unique stereospecific synthesis of a key intermediate developed for the compounds of formula 1.

More explicitly and with reference to one of the preferred groups of compounds of formula 1, mainly the preparation of the compound of formula 1A

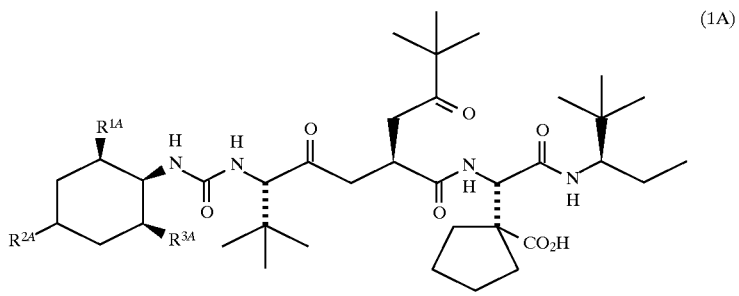

(1A)

wherein $R^{1A}$ is (1-3C)alkyl, $R^{2A}$ is hydrogen or (1-3C)alkyl and $R^{3A}$ is (1-3C)alkyl, this exception is exemplified by the preparation of the key intermediate of formula 2

$$W^1\text{-Tbg-CH}_2\text{-(R)-CH(CH}_2\text{C(O)CMe}_3\text{)C(O)OW}^2 \quad (2)$$

wherein $W^1$ is an amino protective group, and $W^2$ is a carboxyl protective group. In this instance, $W^2$ is a protective group which can be selectively removed in the presence of the protective group $W^1$. Preferably, $W^1$ is tert-butyloxycarbonyl (Boc) or 2,2,2-trichloroethoxycarbonyl and $W^2$ is benzyl, (4-nitrophenyl)methyl, methyl or ethyl.

The intermediate of formula 2 can be prepared by a stereospecific process illustrated in the following Scheme 1.

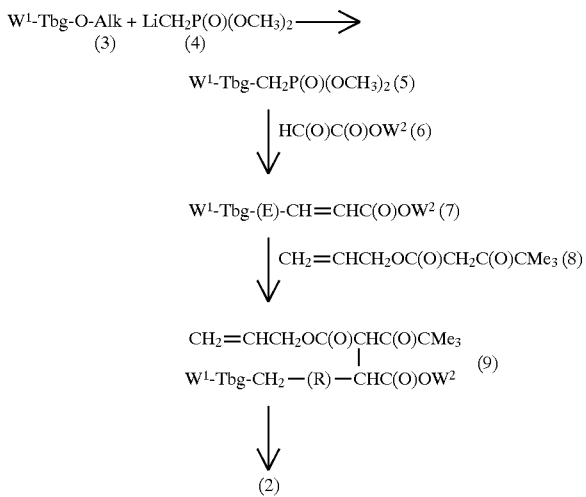

wherein $W^1$ and $W^2$ are as defined herein and Alk is methyl or ethyl.

With reference to the preceding schematic representation, a starting material of formula $W^1$-Tbg-O-Alk (3) is reacted with the reagent $LiCH_2P(O)(OCH_3)_2$ (4) (prepared from $CH_3P(O)(OCH_3)_2$ and butyllithium) to give a phosphonate of formula $W^1$-Tbg-$CH_2P(O)$ $(OCH_3)_2$ (5). Reaction of the latter phosphonate with a glyoxylyl ester of formula $HC(O)C(O)OW^2$ (6) in the presence a suitable tertiary amine, preferably triethylamine or diisopropylethylamine, affords a γ-keto-α,β-unsaturated ester of formula $W^1$-Tbg-(E)-CH=CHC(O)OW$^2$ (7). Reaction of the latter compound with the sodium enolate of a β-ketoester of formula $CH_2$=CHCH$_2$OC(O)CH$_2$C(O)CMe$_3$ (8) affords a Michael adduct of formula $W^1$-Tbg-CH$_2$-(R)-CH{CH(C(O)CMe$_3$)-(C(O)OCH$_2$CH=CH$_2$)}C(O)OW$^2$ (9).

Note (1): The β-ketoester of formula 8, i.e. $CH_2$=CHCH$_2$OC(O)CH$_2$C(O)CMe$_3$, is prepared readily by reacting the lithium enolate of allyl acetate with trimethylacetyl chloride.

Note (2): The sodium enolate of the β-ketoester of formula 8 is generated in situ from the β-ketoester in the presence of a catalytically effective amount of sodium hydride.

Thereafter, reaction of the Michael adduct of formula 9 with tetrakistriphenylphosphine palladium(O) in the presence of a suitable secondary amine, preferably pyrrolidine or piperidine, similar to the method of R. Déziel, Tetrahedron Letters, 28, 4371 (1987), effects deallylation and subsequent decarboxylation of the allyl ester to give the key intermediate of formula 2.

Noteworthy is the unexpected high stereo-selectivity obtained in the Michael addition reaction of the γ-keto-α,β-unsaturated ester of formula 7 with the sodium enolate of the β-ketoester of formula 8 to give the Michael adduct of formula 9. The stereoselectivity of the Michael addition reaction is inferred by the fact that the intermediate of formula 2, derived directly from the Michael adduct, is obtained essentially as a single isomer. The diastereoisomeric purity of the intermediate of formula 2 can be demonstrated by nuclear magnetic resonance studies. The enantiomeric purity of the intermediate of formula 2 can be assessed by removing the amino protective group ($W^1$) and applying the method of J. A. Dale et al., J. Org. Chem., 34, 2543 (1969) to the resulting free amino derivative (see example 4 for more detail).

Thereafter again, the carboxyl protective group ($W^2$) of the key intermediate of formula 2 is selectively removed by standard methods, for example, by hydrogenolysis in the instance wherein $W^2$ is benzyl, to give the corresponding free carboxylic acid derivative (see formula 14 in Scheme 2 below) for incorporation into the process for preparing the compounds of formula 1.

In general, the incorporation of the preceding free carboxylic acid derivative into a process for the preparation of the compounds of formula 1 can be envisaged as a sequence of chemical events wherein a carboxylic acid derivative (representing a first unit) is joined to two other units by first forming an amide bond, and secondly by forming a ureido bond.

In the following more detailed description of a convenient and practical process for preparing the compounds of formula 1, a certain order of the chemical events is followed. However, it will be appreciated that changes in the order of chemical events are not critical and therefore such changes are deemed to be within the scope of the present invention.

Likewise, it should be appreciated that the intermediate of formula 2 wherein protective group $W^1$ can be selectively removed in the presence of protective group $W^2$, allowing for a change in the order of the chemical events, also is deemed to be within the scope of the present invention. Accordingly, an important aspect of this invention includes a key intermediate of formula 2 in which $W^1$ is an amino protective group for the amine at the N-terminus and $W^2$ is a carboxyl protective group for the carboxyl at the C-terminus of the intermediate, with the proviso that the amino protective group $W^1$ can be selectively removed in the presence of the carboxyl protective group $W^2$ when the terminal amine is destined for the reaction to follow, or that, on the other hand, the carboxyl protective group $W^2$ can be selectively removed in the presence of the amino protective group $W^1$ when the terminal carboxyl is destined for the reaction to follow.

Examples of the intermediates of formula 2 wherein the amino protective group $W^1$ can be selectively removed in the presence of the carboxyl protective group $W^2$ include those in which $W^1$ is tert-butyloxycarbonyl and $W^2$ is benzyl, 2,2,2-trichloroethyl, methyl or ethyl.

More particularly, with respect to an overall process, the compounds of formula 1 can be prepared by a convenient and practical process illustrated in the following Scheme 2.

Scheme 2

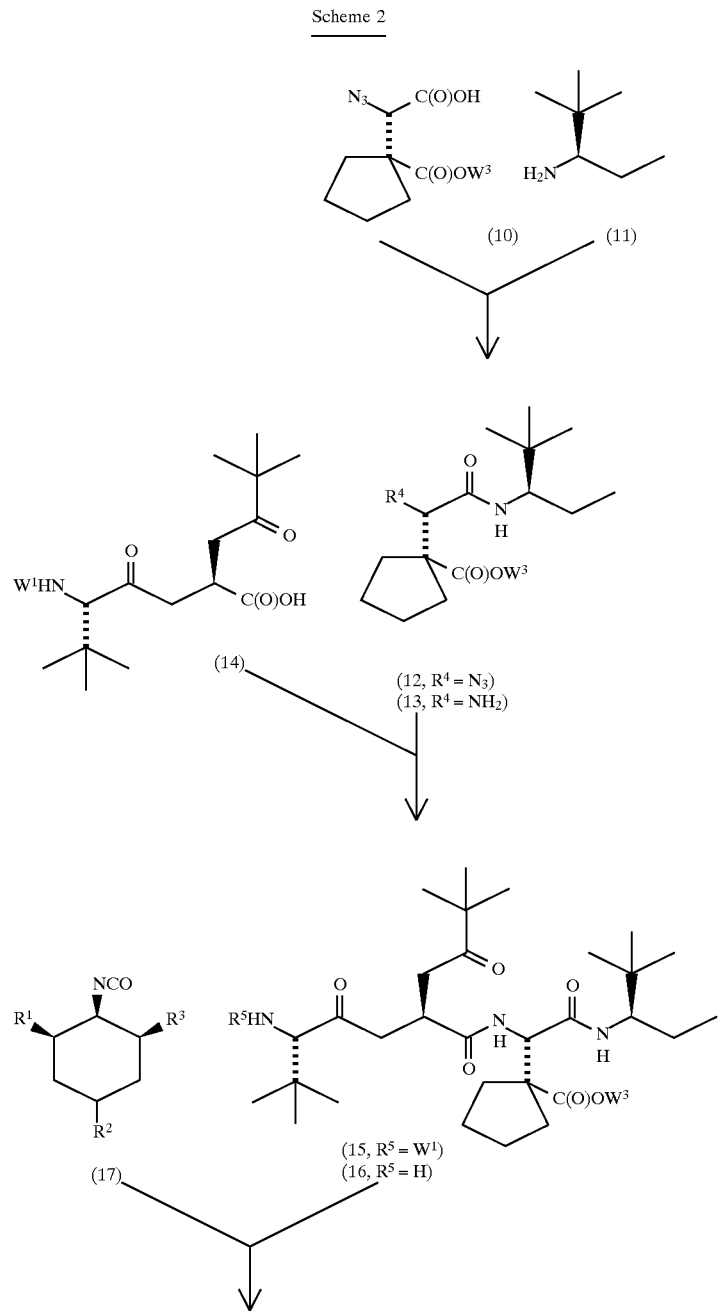

-continued
Scheme 2

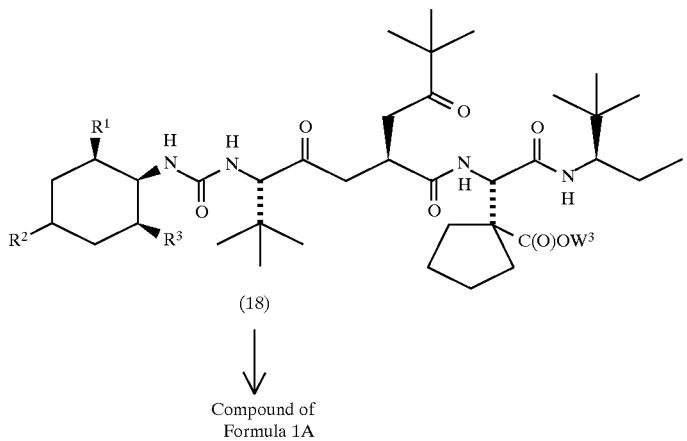

(18)

↓

Compound of
Formula 1A

In Scheme 2, $W^3$ is a carboxyl protective group (preferably benzyl, tert-butyl or 2,2,2-trichloroethyl), $R^4$ is azido for formula 12 and an amino for formula 13, $R^5$ is $W^1$ as defined herein for formula 15 and a hydrogen for formula 16, and $R^1$, $R^2$ and $R^3$ are as defined herein.

Referring to Scheme 2, a process for preparing compound of formula 1 comprises:

(a) coupling a carboxylic acid derivative of formula 10 with an amine of formula 11 to obtain an α-azidoamide of formula 12, (b) reducing the α-azidoamide of formula 12 to obtain a corresponding α-aminoamide of formula 13, (c) coupling the α-amidoamide of formula 13 with a carboxylic acid derivative of formula 14 to obtain a diprotected intermediate of formula 15, (d) selectively deprotecting the diprotected intermediate of formula 15 to obtain the free N-terminal derivative of formula 16, (e) reacting the free N-terminal derivative of formula 16 with an isocyanatocyclohexane derivative of formula 17 to obtain a ureido derivative of formula 18, and (f) deprotecting the latter ureido derivative of formula 18 to obtain the corresponding compound of formula 1, and (g) if desired transforming the compound of formula 1 into a therapeutically acceptable salt thereof.

The coupling steps (a) and (c) and the deprotecting steps (d) and (f) can be achieved by methods commonly used in peptide synthesis.

More explicitly, the coupling step involves the dehydrative coupling of a free carboxyl of one reactant with the free amino group of the other reactant in the presence of coupling agent to form a linking amide bond. Description of such coupling agents are found in general textbooks on peptide chemistry, for example, M. Bodanszky, "Peptide Chemistry", 2nd rev ed, Springer-Verlag, Berlin, Germany, 1993. Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A very practical and useful coupling agent is the commercially available (benzotriazol-1-yloxy)tri(dimethylamino)phosphonium hexafluorophosphate, either by itself or in the presence of 1-hydroxybenzotriazole. Still another very practical and useful coupling agent is commercially available 2-(1H-benzotriazol-1-yl)-N,N,N',N'-tetramethyluronium tetrafluoroborate.

The coupling reaction is conducted in an inert solvent, e.g. dichloromethane or acetonitrile. An excess of a tertiary amine, e.g. diisopropylethylamine or N-methylmorpholine, is added to maintain the reaction mixture at a pH of about eight. The reaction temperature usually ranges between 0° and 50° C. and the reaction time usually ranges between 15 minutes and 24 hours.

In step (b), the azide group of the α-azidoamide of formula 12 is transformed into a corresponding amine of the α-aminoamide of formula 13 by a reducing agent capable of selectively reducing an azide to an amino group in the presence of an amido group and an ester group. This step can be accomplished conveniently and efficiently by the method of N. Maiti et al., Tetrahedron Letters, 27, 1423 (1986) using stannous chloride as the reducing agent and methanol as the reaction solvent.

In step (e), the free N-terminal derivative of formula 16 is reacted directly with a isocyanatocyclohexane derivative of formula 17 to give the ureido derivative of formula 18. This step is based on the classical method for preparing a urea whereby an isocyanato derivative of the residue to be incorporated is reacted with the terminal amino group of an appropriate fragment. {For examples of this method, see P. Majer and R. S. Randad, J. Org. Chem., 59, 1937 (1994).} The reaction proceeds readily in the presence of an excess of a suitable tertiary amine, for example N-methylmorpholine or diisopropylethylamine. The reaction is conducted in an inert solvent, such as dichloromethane or toluene, and at temperatures usually ranging from −20° C. to 20° C.

Furthermore, if desired, the compound of formula 1 can be obtained in the form of a therapeutically acceptable salt. Such salts can be considered as biological equivalents of the compounds of formula 1. Examples of such salts (of the carboxy group) are those formed by known methods with the sodium, potassium or calcium cation.

Antiheroes Activity

The antiviral activity of the compounds of formula 1 can be demonstrated by biochemical, microbiological and biological procedures showing the inhibitory effect of the compounds on the replication of herpes simplex viruses, types 1 and 2 (HSV-1 and HSV-2), as well as acyclovir-resistant herpes simplex viruses.

In the examples hereinafter, the inhibitory effect on herpes ribonucleotide reductase is noted for exemplary compounds of formula 1. Noteworthy, in the connection with this specific inhibition of herpes ribonucleotide reductase, is the relatively minimal effect or absence of such an effect of the compounds on cellular ribonucleotide reductase activity required for normal cell replication.

A method for demonstrating the inhibitory effect of the compounds of formula 1 on viral replication is the cell culture technique; see, for example, T. Spector et al., Proc. Natl. Acad. Sci. USA, 82, 4254 (1985).

The therapeutic effect of the compounds of formula 1 can be demonstrated in laboratory animals, for instance, by using an assay based on the murine model of herpes simplex virus-induced ocular disease for antiviral drug testing, described by C. R. Brandt et al., J. Virol. Meth., 36, 209 (1992).

When a compound of this invention, or one of its therapeutically acceptable acid addition salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the compound, chosen route of administration and standard biological practice. For topical administration, the compound can be formulated in pharmaceutically accepted vehicles containing 0.1 to 5 percent, preferably 0.5 to 5 percent, of the active agent. Such formulations can be in the form of a solution, cream or lotion.

For systemic administration, the compound of formula 1 is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 18th ed, Mack Publishing Company, Easton, Pa., 1990.

The dosage of the compound will vary with the form of administration and the particular active agent chosen. Furthermore, it will vary with the particular host under treatment. Generally, treatment is initiated with small increments until the optimum effect under the circumstances is reached. In general, the compound is most desirably administered at a concentration level that will generally afford antivirally effective results without causing any harmful or deleterious side effects.

With reference to topical application, the compound of formula 1 is administered cutaneously in a suitable topical formulation to the infected area of the body e.g. the skin or part of the oral or genital cavity, in an amount sufficient to cover the infected area. The treatment should be repeated, for example, every four to six hours until lesions heal.

With reference to systemic administration, the compound of formula 1 is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

Another aspect of this invention comprises a cosmetic composition comprising a herpes viral prophylactic amount of the compound of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the compound than corresponding pharmaceutical compositions for topical application. A preferred range of the amount of the compound in the cosmetic composition is 0.5 to 5 percent by weight.

Although the formulations disclosed hereinabove are indicated to be effective and relatively safe medications for treating herpes viral infections, the possible concurrent administration of these formulations with other antiviral medications or agents to obtain beneficial results is not excluded. Such other antiviral medications or agents include the antiviral nucleosides, for example, acyclovir, and antiviral surface active agents or antiviral interferons such as those disclosed by S. S. Asculai and F. Rapp in U.S. Pat. No. 4,507,281, Mar. 26, 1985.

More specifically with respect to treating herpes viral infections by concurrent administration, it has been found that the antiherpes activity of an antiviral nucleoside analogs can be enhanced synergistically, without the concomitant enhancement of toxic effects, by combining the same with a compound of formula 1. Accordingly, there is provided herewith a pharmaceutical composition for treating herpes infections in a mammal comprising a pharmaceutically acceptable carrier, and an effective amount of the combination of an antiviral nucleoside analog or a therapeutically acceptable salt thereof, and a ribonucleotide reductase inhibiting compound of formula 1 or a therapeutically acceptable salt thereof.

Also provided herein is a method of treating herpes viral infections in a mammal. The method comprises administering to the mammal an anti-herpes virally effective amount of a combination of a compound of formula 1 or a therapeutically acceptable salt thereof, and an antiviral nucleoside analog or a therapeutically acceptable salt thereof.

The antiviral nucleoside analog employed in the combination is one which is enzymatically convertible (in vivo) to a viral DNA polymerase inhibitor of, and/or an alternative substrate for, a herpes DNA polymerase. The antiviral nucleoside analog can be selected from known nucleoside analogs. Preferred nucleoside analogs of the invention include acyclovir and its analogs; for example, the compounds of formula 19

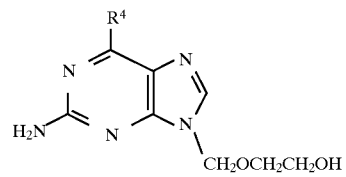

(19)

wherein $R^4$ is hydrogen, hydroxy or amino, or a therapeutically acceptable salt thereof. (Formula 19 wherein $R^4$ is hydroxy represents acyclovir.)

Other preferred antiviral nucleoside analogs for use according to the present invention include penciclovir, famciclovir and valacyclovir.

An example of a therapeutically acceptable salt of the nucleoside analogs is the sodium salt.

The term "synergistic effect" when used in relation to the antiviral or antiherpes activity of the above defined combination of the nucleoside analog and the compound of formula 1 means an antiviral or antiherpes effect which is greater than the predictive additive effect of the two individual components of the combination.

When utilizing the combination of this invention for treating herpes infections, the combination is administered to warm blooded animals, e.g. humans, pigs or horses, in a vehicle comprising one or more pharmaceutically acceptable carriers, the proportion of which is determined by the solubility and chemical nature of the nucleoside analog and the compound of formula 1, chosen route of administration, standard biological practice, and by the relative amounts of the two active ingredients to provide a synergistic antiviral effect. The combination may be administered topically. For example, the two active agents (i.e. the antiviral nucleoside analog and the compound of formula 1, or their therapeutically acceptable salts) can be formulated in the form of solutions, emulsions, creams, or lotions in pharmaceutically acceptable vehicles. Such formulation can contain 0.01 to 1.0 percent by weight of the nucleoside analog, or a therapeutically acceptable salt thereof, and about 0.05 to 1 percent by weight of the compound of formula 1, or a therapeutically acceptable salt thereof.

In any event, the two active agents are present in the pharmaceutical composition in amounts to provide a synergistic antiherpes effect.

The following examples illustrate further this invention. Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 200 MHz or 400 MHz spectrometer (a 200 MHz spectrum being noted in th e preamble); the chemical shifts ($\delta$) are reported in parts per million. Abbreviations used in the examples include Boc: tert-butyloxycarbonyl; Bu: butyl; Bzl: benzyl; DMF: dimethylformamide; DMSO: dimethylsulfoxide; Et: ethyl; EtOH: ethanol; EtOAc: ethyl acetate; Et$_2$O: diethyl ether; HPLC: high performance liquid chromatography; Me: methyl; MeOH: methanol; Pr: propyl; TLC: thin layer chromatography; THF: tetrahydrofuran.

EXAMPLE 1

General Procedure for Coupling Reactions

{See also R. Knorr et al., Tetrahedron Letters, 30, 1927 (1989).}

The first reactant, i.e. a free amine (or its hydrochloride salt), is dissolved in CH$_2$Cl$_2$ or CH$_3$CN and the solution is cooled to 4°. Under a n itrogen atmosphere, four equivalents of N-methylmorpholine are added to the stirred solution. After 20 min, one equivalent of the second reactant, i.e. a free carboxylic acid, and 1.05 equivalents of the coupling agent are added. (Practical and efficient coupling reagents for this purpose are (benzotriazol-1-yloxy)tris-(dimethylamino)phosphonium hexafluorophosphate or preferably 2-(1H-benzotriazol-1-yl) -N,N,N',N'-tetramethyluronium tetrafluoroborate. The reaction is monitored by TLC. After completion of the reaction, the solvent is evaporated under reduced pressure. The residue is dissolved in EtOAc. The solution is washed successively with 1N aqueous citric acid, 10% aqueous Na$_2$CO$_3$ and brine. The organic phase is dried (MgSO$_4$), filtered and concentrated under reduced pressure. The residue is purified on silica gel (SiO$_2$) according to Still's flash chromatography technique {W. C. Still et al., J. Org. Chem., 43, 2923 (1978)}.

EXAMPLE 2

Preparation of the Intermediate H-Asp(cyPn)(Bzl)-NH-(S)-CH(CH$_2$CMe$_3$)CH$_2$OBzl (a) (S)-$\alpha$-Azido-1-{(phenylmethoxy)carbonyl}-cyclopentaneacetic acid: This compound was prepared from 2-oxospiro[4.4]nonane-1,3-dione, described by M. N. Aboul-Enein et al., Pharm. Acta Helv., 55, 50 (1980), according to the asymmetric azidation method utilizing the Evan's auxiliary, see D. A. Evans et al., J. Amer. Chem. Soc., 112, 4011 (1990).

More explicitly, a 1.6M hexane solution of butyllithium (469 mL, 750 mmol) was added dropwise under an argon atmosphere to a solution of the chiral auxiliary, 4(S)-(1-methylethyl)-2-oxazolidinone, (96.8 g, 750 mmol) {described by L. N. Pridgen and J. Prol., J. Org, Chem, 54, 3231 (1989)} in dry THF at −40°. The mixture was stirred at −40° for 30 min and then cooled to −78°. 2-Oxospiro [4.4]nonane-1,3-dione was added dropwise to the cooled mixture. The mixture was stirred at 0° for 1 h. Thereafter, a 20% aqueous solution of citric acid (600 mL) was added to the mixture. The organic phase was separated and the aqueous phase was extracted with EtOAc. The combined organic phases were washed with brine, dried (MgSO$_4$) and concentrated under reduced pressure to give 3-[2-(1-carboxycyclopentyl)- 1-oxoethyl)}-4(S)-(1-methylethyl)-2-oxazolidinone as a pink solid (300 g).

The latter solid (ca 750 mmol) was dissolved in CH$_3$CN (1 L). Benzyl bromide (89.2 mL, 750 mmol) and 1,8-diazabicyclo[5.4.0]undec-7-ene (112 mL, 750 mmol) were added to the solution. The mixture was stirred under argon for 16 h. The volatiles were removed under reduced pressure. The residue was dissolved in H$_2$O/EtOAc. The organic phase was separated, washed with a 10% aqueous solution of citric acid and brine, dried (MgSO$_4$) and concentrated under reduced pressure to give an oil. Crystallization of the oil from hexane/EtOAc gave the corresponding benzyl ester as a white solid (204 g, 73% yield).

A solution of the latter compound (70 g, 190 mmol) in dry THF (200 mL) was cooled to −78°. A 0.66M THF solution of potassium bis(trimethylsilyl)amide (286 mL, 190 mmol) containing 6% cumene was added over a period of 15 min to the cooled solution. The mixture was stirred at −78° for 45 min. A solution of 2,4,6-triisopropylbenzenesulfonyl azide (67 g, 220 mmol) in dry THF (100 mL) was added in one portion to the cold mixture, followed two minutes later by the addition of glacial acetic acid (50 mL, 860 mmol). The mixture was warmed and stirred at 35°–45° for 1 h. The volatiles were removed under reduced pressure. The yellow residue was triturated with hexane/EtOH (4:1, 1.7 L). The resulting white solid was collected on a filter. The filtrate was mixed with SiO$_2$ (230–240 mesh). Volatiles were removed under reduced pressure and the residual solid was dried at 35° under reduced pressure to remove cumene. The residual solid then was placed on a column of SiO$_2$. Elution of the column with hexane-EtOAc (9:1) and concentration of the eluent gave 3-{(2(S)-azido-1-oxo-2-{1-{(phenylmethoxy)carbonyl}cyclopentyl}-ethyl}-4(S)-(1-methylethyl)-2-oxazolidinone (66 g, 86% yield).

A solution of the latter compound (13.4 g, 32.4 mmol) in THF/H$_2$O (3:1, 608 mL) was cooled to 0°. Hydrogen peroxide/H$_2$O (3:7, 16.3 mL, 141 mmol of H$_2$O$_2$) was added to the cooled solution, followed by the addition of LiOH.H$_2$O (2.86 g, 68.2 mmol). The mixture was stirred at 0° for 45 min and then quenched with a 10% aqueous solution of sodium sulfite (400 mL). After NaHCO$_3$ (1.93 g) had been added, the mixture was concentrated under reduced pressure. The chiral auxiliary was recovered by continuous extraction (aqueous NaHCO$_3$/chloroform) for 20 h. Thereafter, the aqueous phase was cooled to 0° rendered acidic by the addition of concentrated HCl and then extracted with EtOAc. The extract was washed with brine, dried (MgSO$_4$) and concentrated under reduced pressure to give (S)-α-azido-1-{(phenylmethoxy)carbonyl}cyclopentaneacetic acid as a white solid (8.2 g, 84% yield). $^1$H NMR (CDCl$_3$) δ7.40–7.28 (m, 5H), 5.12 (s, 2H), 4.55 (s, 1H), 2.30–2.20 (m, 1H), 2.05–1.95 (m, 2H), 1.8–1.6 (m, 5H).

The compound is used in section (c) of this example.

(b) NH$_2$-(S)-CH(CH$_2$CMe$_3$)CH$_2$OBzl: H-γMeLeu-OH was reduced with LiBH$_4$/Me$_3$SiCl according to the method of A. Giannis and K. Sandhoff, Angew. Chem. Int. Ed. Engl., 28, 218 (1989) to give the aminoalcohol NH$_2$-(S)-CH(CH$_2$CMe$_3$)CH$_2$OH. A mixture of the latter compound (812 mg, 6.2 mmol), triethylamine (659 mg, 6.51 mmol) and di-tert-butyl dicarbonate (1.42 g, 6.51 mmol) in dry THF (15 mL) was stirred under a nitrogen atmosphere at 4° for 15 min and then at room temperature for 4 h. The THF was evaporated under reduced pressure. The residue was dissolved in EtOAc. The solution was washed with 10% aqueous citric acid, 5% aqueous NaHCO$_3$ and brine. The organic phase was dried (MgSO$_4$) and concentrated to dryness under reduced pressure. The residue was purified by flash chromatography (SiO$_2$, eluent: hexane-EtOAc, 2:1) to give Boc-NH-(S)-CH(CH$_2$CMe$_3$)-CH$_2$OH (1.23 g, 86%).

Tetrabutylammonium bisulfate (106 mg) and 50% aqueous NaOH (3 mL) were added successively to a solution of Boc-NH-(S)-CH(CH$_2$CMe$_3$)CH$_2$OH (1.23 g, 5.35 mmol) in benzyl chloride (13 mL). The resulting mixture was stirred at 35°–40° for 90 min, diluted with EtOAc, and washed with H$_2$O and brine. The organic phase was dried (MgSO$_4$) and concentrated to dryness under reduced pressure. The residue was dissolved in hexane. The solution was poured onto a column of SiO$_2$. The column was eluted with hexane to remove benzyl chloride, and then with hexane-EtOAc (2:1) to give Boc-NH-(S)-CH(CH$_2$CMe$_3$)CH$_2$OBzl. The $^1$H NMR (CDCl$_3$), 200 MHz, of the latter compound showed δ0.95 (s,9H), 1.42 (s, 9H), 1.30–1.55 (m, 2H), 3.42 (d, J=4 Hz, 2H), 3.88 (broad, 1H), 4.54 (m, 3H), 7.23–7.4 (m, 5H). The latter compound (1.28 g, 3.99 mmol) was dissolved in 6N HCl/dioxane (10 mL). The solution was stirred under a nitrogen atmosphere at 4° for 45 min. Evaporation of the solvent gave the hydrogen chloride salt of the desired compound (1.05 g). The compound is used without further purification in the next section of this example. (c) The title compound of this example: By following the coupling procedure of example 1 and using the hydrogen chloride salt of NH$_2$-(S)-CH(CH$_2$CMe$_3$)CH$_2$OBzl of the preceding section as the first reactant and (S)-α-azido-1-{(phenylmethoxy)carbonyl}cyclopentaneacetic acid of section (a) of this example as the second reactant, N-{(S)-1-benzyloxymethyl-3,3-dimethylbutyl}-(S)-α-azido-1-{(phenylmethoxy)carbonyl} cyclopentaneacetamide was obtained. Reduction of the latter compound with tin(II) chloride in MeOH according to the method of N. Maiti et al., Tetrahedron Letters, 27, 1423 (1986) gave the title compound of this example. The $^1$H NMR (CDCl$_3$), 200 MHz, of the compound showed δ0.98 (s, 9H), 1.22–2.25 (m, 12H), 3.4 (d, J=4 Hz, 2H), 3.64 (s, 1H), 4.18 (broad m, 1H), 4.52 (s, 2H), 5.12 (s, 2H), 7.18 (d, J=7 Hz, 1H), 7.22–7.38 (broad m, 10H).

EXAMPLE 3

Preparation of the Intermediate Boc-Tbg-CH$_2$-(RS)-CH(CH$_2$C(O)CMe$_3$)C(O)OH (a) Magnesium salt of monoallyl malonate: A solution of 2,2-dimethyl-1,3-dioxane-4,6-dione (100 g, 0.69 mol) and allyl alcohol (47 mL, 0.69 mol in benzene (800 mL) was heated at reflux for 24 h. The solvent was evaporated under reduced pressure. Distillation of the residue under reduced pressure gave monoallyl malonate (71 g, 71%, bp 123°–127°/2.7 mm Hg). The latter ester (71 g, 0.48 mol) was dissolved in dry THF (300 mL). Magnesium ethoxide (28.5 g, 0.245 mol) was added to the solution. The mixture was stirred under argon for 4 h at room temperature (20°–22°). The solvent was evaporated under reduced pressure and the residue was triturated with Et$_2$O to give a tan solid. The solid was ground into fine particles and dried under reduced pressure to give the desired magnesium salt (56 g, 73%). The salt is used in the next section of this example.

(b) Boc-Tbg-CH$_2$C(O)OCH$_2$=CH$_2$: 1,1-Carbonyldiimidazole (12.6 g, 78 mmol) was added to a solution of Boc-Tbg-OH (15 g, 64 mmol) in dry acetonitrile (150 mL). The mixture was stirred under argon for 2 h at room temperature. The magnesium salt of monoallyl malonate (24 g, 78 mmol) and 4-(N,N-dimethylamino)pyridine (100 mg) were added to the mixture. The mixture was heated at reflux for 1 h and then stirred at room temperature for 18 h. Thereafter, the mixture was concentrated under reduced pressure. The residue was dissolved in EtOAc (300 mL). The solution was washed with 10% aqueous citric acid (2×100 mL) and brine (2×100 mL), dried (MgSO$_4$) and evaporated to dryness. The residue was purified by flash chromatography (SiO$_2$, eluent: hexane-EtOAc, 9:1) to give the desired allyl ester (19.4 g, 96%) as a brown oil which crystallized on standing. $^1$H NMR (CDCl$_3$), 200 MHz, note that this compound exists as a mixture of keto-enol tautomers in a 3:1 ratio in chloroform, δ0.96 (s, 9H, enol form), 1.04 (s, 9H), 1.46 (s, 9H), 3.65 (s, 2H), 3.90 (d, J=8.5 Hz, 1H, enol form), 4.20 (d, J=7.5 Hz, 1H), 4.65 (m, 2H), 5.10 (broad d, J=7.5 Hz, 1H), 5.20–5.40 (m, 2H), 5.80–6.05 (m, 1H), 12 (s, 1H, enol form). The allyl ester is used in section (d) of this example.

(c) (E)-5,5-Dimethyl-4-oxo-2-hexenoic acid ethyl ester: This ethyl ester was prepared according to the method of S. Manfredini et al., Tetrahedron Letters, 29, 3997 (1988). The oily crude product was purified by flash chromatography (SiO$_2$, eluent: hexane) to give the desired ethyl ester as a yellow oil. $^1$H NMR (CDCl$_3$), 200 MHz, δ1.21 (s, 9H), 1.33 (t, J=7.5 Hz, 3H), 4.28 (q, J=7.5 Hz, 2H), 6.78 (d, J=15.5 Hz, 1H), 7.51 (d, J=15.5 Hz, 1H). The ethyl ester is used in the next section of this example.

(d) The title compound of this example: Boc-Tbg-CH$_2$C(O)OCH=CH$_2$ (0.67 g, 2.1 mmol), described in section (b) of this example, was dissolved in anhydrous THF (25 mL) under an argon atmosphere. Sodium hydride (60% oil dispersion, 0.095 g, 2.4 mmol) was added to the solution. The mixture was stirred at room temperature for 30 min. (E)-5,5-dimethyl-4-oxo-2-hexenoic acid ethyl ester (0.435 g, 2.36 mmol), described in section (c) of this example, was added to the mixture. The reaction mixture was stirred until the reaction was complete as judged by TLC (about 6 h). Thereafter, the mixture was quenched with 10% aqueous citric acid. THF was removed under reduced pressure and the resulting concentrate was extracted with EtOAc (3×25 mL). The extract was washed with H$_2$O, dried (MgSO$_4$) and concentrated under reduced pressure. The residue was purified by flash chromatography (SiO$_2$, eluent: hexane-EtOAc, 9:1) to give the corresponding Michael reaction adduct (1.06 g, 100%).

The Michael adduct was transformed to Boc-Tbg-CH$_2$-(RS)-CH(CH$_2$C(O)CMe$_3$)C(O)OH as follows: Tetrakistriphenylphosphine palladium(O) (0.20 g, 0.18 mmol) and triphenylphosphine (0.060 g, 0.23 mmol) were dissolved in CH$_2$Cl$_2$ (10 mL) under an argon atmosphere. Acetonitrile (20 mL) was added and the solution was cooled to 0°.

Pyrrolidine (0.28 mL, 2.7 mmol) and then the Michael adduct (1.06 g, 2.1 mmol) were added to the solution. The mixture was allowed to come to room temperature over 1 h and then stirred for 20 h. Thereafter, the reaction mixture was heated at reflux for 1 h under argon to complete the reaction. The solvent was evaporated and the residue was purified by flash chromatography ($SiO_2$, eluent: hexane-EtOAc, 9:1) to give Boc-Tbg-$CH_2$-(RS)-CH($CH_2$C(O) $CMe_3$)C(O)OEt (0.77 g, 83%). Thereafter, the latter compound (0.77 g, 1.7 mmol) was dissolved in ethyleneglycol dimethyl ether —$H_2O$ (1:1, 10 mL). Lithium hydroxide monohydrate (0.31 g, 7.4 mmol) was added to the solution. The mixture was stirred at room temperature for 4 h, rendered acidic with 10% aqueous citric acid (20 mL) and extracted with EtOAc (3×25 mL). The extract was dried ($MgSO_4$) and concentrated under reduced pressure to give the title compound of this example as a tan solid (0.69 g, 80% yield overall from Boc-Tbg-$CH_2$C(O)O-$CH_2$CH=$CH_2$). The product was a 55:45 mixture of diastereoisomers (shown by NMR). $^1$H NMR ($CDCl_3$), 200 MHz, δ0.99 (s, 9H, minor isomer), 1.14 (s, 9H, major isomer), 1.43 (s, 9H), 2.68–3.12 (m, 4H), 3.30 (m, 1H), 4.09 (d, J=9 Hz, 1H), 5.11 (d, J=9 Hz, 1H).

EXAMPLE 4

Preparation of the Intermediate H-Tbg-$CH_2$CH ($CH_2$C(O)$CMe_3$)C(O)-Asp(cyPn)(Bzl)-NH-(S)-CH ($CH_2CMe_3$) $CH_2$OBzl By following the coupling procedure of example 1 and using the title compound of example 2(3.42 g, 7.13 mmol) as the first reactant and the title compound of example 3 (2.50 g, 6.48 mmol) as the second reactant, flash chromatography ($SiO_2$, eluent: hexane-EtOAc, 4:1) of the crude product gave the corresponding N-Boc derivative of the title compound (4.64 g, 84%; Rf=0.21, hexane-EtOAc, 7:3). A solution of the latter derivative (4.64 g, 5.44 mmol) in 6N HCl/dioxane (50 mL) was stirred at room temperature for 1 h and then concentrated under reduced pressure. The residue was dissolved in $Et_2O$. The latter solution was washed with saturated aqueous solution of $NaHCO_3$ and brine, dried ($MgSO_4$) and concentrated to give a yellow oil consisting of two diastereoisomers. The two isomers were separated by flash chromatography ($SiO_2$, eluent: hexane-EtOAc-MeOH, 5:4.5:0.5). The desired isomer (i.e. the more polar; Rf =0.18, EtOAc-hexane-MeOH, 7:3:0.5) was obtained as a colourless oil (2.52 g, 52%). The isomer, the title compound of this example, is used without further purification in the next example.

EXAMPLE 5

Preparation of Boc-(N-Me)Val-Tbg-$CH_2$(R)-CH ($CH_2$C(O)$CMe_3$)C(O)-Asp(cyPn)(Bzl)-NH-(S)-CH ($CH_2CMe_3$)$CH_2$OBzl By following the coupling procedure of example 1 and using the title compound of example 4(4.45 g, 5.95 mmol) as the first reactant and Boc-(N-Me)-Val-OH (4.41 g, 17.9 mmol) as the second reactant, flash chromatography ($SiO_2$, eluent: hexane-EtOAc, 7:3) of the crude product gave the title compound of this example (4.02 g, 72% yield). $^1$H NMR ($CDCl_3$), 200 MHz, δ0.87 (d, J=7 Hz, 6H), 0.90 (s, 18H), 1.10 (s, 9H), 1.48 (s, 9H), 1.5–2.0 (m, 10H), 2.30 (m, 1H), 2.5–3.1 (m, 5H), 2.80 (s, 3H), 3.30 (m, 2H), 4.0 (d, J=12.5 Hz, 1H), 4.20 (m, 1H), 4.32 (d, J=8.5 Hz, 1H), 4.49 (d, J=4.5 Hz, 2H), 4.64 (d, J=11 Hz, 1H), 5.18 (d, J=5 Hz, 2H), 6.78 (broad d, J=8.5 Hz, 1H), 7.11 (broad d, J=8.5 Hz, 1H), 7.18 (broad d, J=11 Hz, 1H), 7.2–7.45 (m, 10H).

EXAMPLE 6

Preparation of $PhCH_2CH_2$C(O)-(N-Me)Val-Tbg-$CH_2$-(R)-CH($CH_2$C (O) $CMe_3$) C (O)-Asp (cyPn)-γMeLeucinol A solution of the title compound of example 5 (4.02 g, 4.25 mmol) in 6N HCl/dioxane (30 mL) was stirred at room temperature for 1 h and then concentrated under reduced pressure to give the free N-terminal amino derivative of the title compound of example 5 in the form of its hydrochoride salt. Thereafter, by following the coupling procedure of example 1 and using the latter amino derivative as the first reactant and benzenepropionic acid (2.00 g, 13.3 mmol) as the second reactant, the purification of the crude product by flash chromatography ($SiO_2$, eluent: hexane-EtOAc, 3:2) gave $PhCH_2CH_2$C(O)-N-Me-Val-Tbg-$CH_2$-(R)-CH($CH_2$C (O)$CMe_3$)C(O)-Asp(cyPn) (OBzl)-NH-(S)-CH($CH_2CMe_3$) $CH_2$OBzl as a white foam (4.00 g, 94%; Rf=0.35, hexane-EtOAc, 1:1). $^1$H NMR ($CDCl_3$) δ0.79 (d, J=7 Hz, 3H), 0.91 (s, 9H), 0.93 (s, 9H), 1.08 (s, 9H), 1.5–1.9 (m, 10H), 2.27 (m, 1H), 2.5–2.85 (m, 7H), 2.90 (s, 3H), 2.97 (m, 4H), 3.27 (dd, J=11, 7 Hz, 1H), 3.55 (dd, J=11, 4.5 Hz, 1H), 3.48 (q, J=7.5 Hz, 2H), 4.22 (m, 1H), 4.27 (d, J=8 Hz, 1H), 4.48 (q, J=8.5 Hz, 2H), 4.53 (d, J=11 Hz, 1H), 4.63 (d, J=0.5 Hz, 1H), 5.16 (q, J=13 Hz, 2H), 6.72 (d, J=8 Hz, 1H), 7.02 (d, J=8.5 Hz, 1H), 7.17 (d, J=9.5 Hz, 1H), 7.18–7.4 (m, 10H).

The latter compound (4.00 g, 4.03 mmol) was subjected to hydrogenolysis {20% Pd(OH)$_2$/C (200 mg), 1 atmosphere of $H_2$, EtOH, 5 h}. After completion of the reaction, the catalyst was removed from the reaction mixture by filtration through a 45 μm membrane. The filtrate was concentrated under reduced pressure to give a clear oil. The oil was dissolved in $Et_2O$ (100 mL). The solution was evaporated to dryness under reduced pressure. The dissolving and evaporating process was repeated whereby a white solid was obtained. The solid was triturated with hexane, filtered and dried under reduced pressure to give the title compound (3.12 g, 95%) $^1$H NMR (d6-DMSO); note: the compound exists in DMSO as a 50:50 mixture of two rotamers δ0.71–0.92 (m, 24H), 1.05 (s, 4.5H), 1.06 (s, 4.5H), 1.20–1.78 (m, 10H), 1.93–2.16 (m, 2H), 2.48–2.83 (m, 6H), 2.84 (s, 1.5H), 2.92 (s, 1.5H), 2.96–3.06 (m, 1H), 3.10–3.23 (m, 2H), 3.72–3.81 (m, 1H), 4.09–4.14 (m, 1H), 4.22 (d, 8 Hz, 0.5H), 4.54–4.62 (broad m, 1H), 4.73–4.81 (m, 1.5H), 7.12–7.29 (m, 6H), 7.94 (d, J=10 Hz, 1H), 8.04 (d, J=8 Hz, 0.5H), 8.32 (d, J=8.5 Hz, 0.5H).

By following the procedure of example 6 but replacing benzenepropionic acid with 2-(phenylmethyl)-3-phenylpropionic acid (dibenzylacetic acid), $(PhCH_2)_2$CHC (O)-(N-Me)Val-Tbg-$CH_2$-(R)-CH($CH_2$C(O)-$CMe_3$)C(O)-Asp(cypn)-γMeLeucinol is obtained.

EXAMPLE 7

Preparation of $Et_2$CHNHC(O)-Tbg-$CH_2$-(R)-CH ($OH_2$C(O)$CMe_3$)CO-Asp(cyPn)-γMeLeucinol 1-Ethylpropyl isocyanate (28 mg, 0.248 mmol) was added to a solution of the title compound of example 4 (23 mg, 0.030 mmol) and triethylamine (6 mg, 0.057 mmol) in anhydrous $CH_2Cl_2$. The reaction mixture was stirred under an argon atmosphere at 0° for 1 h and then at room temperature for 18 h. TLC (EtOAc-hexane, 1:1) indicated the completion of the reaction. The solvent was evaporated under reduced pressure. The residue was purified by flash chromatography ($SiO_2$, eluent: hexane-EtOAc, 6:4) to give the corresponding dibenzyl derivative of the title compound of this example (16 mg). $^1$H NMR (CDCl$_3$) δ0.9 (t, J=7 Hz, 3H), 0.92 (t, J=7 Hz, 3H), 0.94 (s, 9H), 0.95 (s, 9H), 1.10 (s, 9H), 1.25–1.90 (m, 14H), 2.52 (m, 1H), 2.68 (m, 1H), 2.81 (m, 1H), 2.94–3.07 (m, 2H), 3.27 (dd, J=7.2, 9 Hz, 1H), 3.36 (dd, J=5.5, 9 Hz, 1H), 3.46 (m, 1H), 4.07 (d, J=9 Hz, 1H), 4.23 (m, 1H), 4.28 (d, J=9 Hz, 1H), 4.48 (dd, J=10 Hz, 2H), 4.66 (d, J=10 Hz, 1H), 4.74 (d, J=9 Hz, 1H), 5.17 (dd, J=14 Hz, 2H), 7.10 (d, J=8.5 Hz, 1H), 7.2–7.45 (m, 11H).

The latter dibenzyl derivative was subjected to hydrogenolysis (10% palladium on carbon, 1 atmosphere, EtOH) to give the title compound. Mass spectrum: 703 (M+Na)$^+$.

EXAMPLE 8

Preparation of Other Representative Intermediates for the Elaboration of the C-Terminus of Peptides of Formula 1

(a) NH$_2$-(R)-CH(Et)CMe$_3$: To a cooled solution (0°) of 4,4-dimethyl-3-pentanone (106 g, 0.928 mol) and (R)-α-methylbenzylamine (111 g, 0.916 mol) in benzene (1 L), a solution of TiCl$_4$ (50.5 mL, 0.461 mol) in benzene (200 mL) was added at a rate that kept the temperature of the mixture below 10°. Thereafter, the mixture was stirred mechnically for 3 h at 40°, cooled to room temperature and filtered through diatomaceous earth. The diatomaceous earth was washed with Et$_2$O. The combined filtrate and wash was concentrated. The residue was dissolved in dry MeOH (2 L). The solution was cooled to 0° and NaBH$_4$ (20 g, 0.53 mol) was added portionwise while maintaining the temperature of the mixture below 5°. The methanol was evaporated. The residue was dissolved in Et$_2$O. The solution was washed with brine, dried (MgSO$_4$) and concentrated to give a reddish oil (a 18:1 mixture of diastereoisomers as indicated by NMR). The oil was purified by flash chromatography (SiO$_2$, eluent: EtOAc/hexane, 7:93) to afford N-(1(R)-phenylethyl)-1(R)-ethyl-2,2-dimethylpropylamine as a liquid (110 g, 54% yield). This material was dissolved in hexane (1.5 L). 1N HCl in Et$_2$O (550 mL) was added to the solution over a period of 15 min. The resulting white solid was collected on a filter and then washed with hexane to provide N-(1(R)-phenylethyl)-1(R)-ethyl-2,2-dimethylpropylamine hydrochloride (125 g, 97% yield). $^1$H NMR(CDCl$_3$) δ7.79–7.74 (m, 2H), 7.48–7.30 (m, 3H), 4.49–4.31 (m, 1H), 2.44–2.36 (m, 1H), 2.23 (d, J=6.5 Hz, 3H), 1.95–1.54 (m, 2H), 1.14 (s, 9H), 0.55 (t, J=7.5 Hz, 3H).

A solution of the latter compound (41.5 g) in MeOH (120 mL) was mixed with 10% Pd/C (w/w) (4.2 g) and the mixture was shaken under 50 psi of hydrogen in a Parr hydrogenator at room temperature for 48 h. The mixture was filtered through diatomaceous earth and the filtrate was concentrated to give the desired NH$_2$-(R)-CH(Et)CMe$_3$ in the form of its hydrochloric acid addition salt, as a white solid (25 g, 100% yield). $^1$H NMR(CDCl$_3$) δ8.40–8.10 (broad s, 3H), 2.85–2.70 (m, 1H), 1.90–1.58 (m, 2H), 1.22 (t, J=7 Hz, 3H), 1.10 (s, 9H).

In the same manner but replacing 4,4-dimethyl-3-pentanone with 3,3-dimethyl-2-butanone in the preceding procedure, NH$_2$-(R)-CH(Me)CMe$_3$.HCl is obtained.

(b) NH$_2$N(Me)CMe$_3$: NaOH (3.3 g, 82 mmol) was added to a solution of tert-butylhydrazine hydrochloride (5.1 g, 41 mmol). After 15 min, a solution of di-tert-butyl dicarbonate (9.0 g, 42 mmol) in THF (15 mL) was added to the mixture. The mixture was stirred at room temperature for 15 h and then extracted with Et$_2$O (3×20 mL). The combined extracts were washed with a saturated aqueous solution of Na$_2$CO$_3$, dried (MgSO$_4$) and concentrated to afford a white solid (7.6 g). The latter material (1.3 g, 6.9 mmol) was dissolved in dry DMF. A 60% (w/w) dispersion of NaH in mineral oil (0.28 g, i.e. 6.9 mmol of NaH) and then DMF (1.5 mL) were added to the solution. After the mixture had been stirred for 20 min, neat methyliodide (0.97 g, 6.9 mmol) was added. The reaction mixture was stirred at room temperature for 15 h and then partitioned between H$_2$O and Et$_2$O. The organic phase was separated and washed with 0.5N aqueous HCl (2 X). The combined aqueous phases were rendered basic with NaHCO$_3$ and extracted with EtOAc (3 X). The EtOAc extract was dried (MgSO$_4$) and concentrated to dryness to afford Boc-NHN(Me)CMe$_3$ as a white solid (0.9 g, 64%); $^1$H NMR(CDCl$_3$) δ1.07 (s, 9H), 1.44 (s, 9H), 2.43 (s, 3H), 5.29 (s, 1H). The latter solid (0.9 g) was dissolved in 6 N HCl/dioxane (5 mL). The solution was allowed to stand at room temperature for 30 min and then concentrated to dryness. Trituration of the residue with hexane afforded NH$_2$N(CH$_3$)CMe$_3$.HCl as a white solid (0.5 g).

In the same manner but replacing methyl iodide with ethyl iodide in the preceding procedure, NH$_2$N(Et)-CMe$_3$.HCl, mp 129°–134°, is obtained.

EXAMPLE 9

Preparation of Other Representative Intermediates for Elaborating the N-Terminus of Peptides of Formula 1 According to the Procedure of Example 7

(a) 1-Propylbutyl isocyanate: This intermediate was prepared from commercially available 4-aminoheptane by the procedure of V. S. Goldesmidt and M. Wick, Liebigs Ann. Chem., 575, 217 (1952). (b) 1-Ethyl-1-(2-propenyl)-3-butenyl isocyanate: A solution of propionitrile (14.5 g, 264 mmol) in dry Et$_2$O (40 mL) was added dropwise to 1.0M allyl magnesium bromide/Et$_2$O (880 mL). The reaction mixture was mechanically stirred at reflux for 2 h, after which time it was cooled to 0°. A saturated aqueous solution of NH$_4$Cl (320 mL) was added cautiously to the cooled reaction mixture. The organic phase was separated, dried (MgSO$_4$), cooled to 0° and then mixed at the same temperature with 1M HCl/Et$_2$O (200 mL). The resulting solid was collected and dried under reduced pressure (ca 27 g). The latter material dissolved in CH$_2$Cl$_2$ (200 mL). The solution was washed with a 10% aqueous solution of Na$_2$CO$_3$ (2 X) and then brine, dried (MgSO$_4$) and concentrated to dryness to afford a yellow oil. The oil was distilled (82°–85°/20 Torr) to give 1-ethyl-1-(2-propenyl)-3-butenylamine as a colorless liquid (11.6 g, 34%); $^1$H NMR (CDCl$_3$) δ0.89 (t, J=7Hz, 3H), 1.39 (q, J=7 Hz, 2H), 2.11 (d, J=7 Hz, 2H), 5.06–5.14 (m, 4H), 5.80–5.89 (m, 2H).

The latter compound was converted to 1-ethyl-1-(2-propenyl)-3-butenyl isocyanate by the procedure of V. S. Goldesmidt and M. Wick, supra.

The first step of the process of preceding section b, i.e. the preparation of 1-ethyl-1-(2-propenyl)-3-butenylamine, is based on a general method described by G. Alvernhe and A. Laurent, Tetrahedron Lett., 1057 (1973). The overall process, with the appropriate choice of reactants, can be used to prepare other requisite isocyanate intermediates for the eventual preparation of peptides of formula 1 having unsaturation at the N-terminus, i.e. peptides of formula 1 wherein A-B is an unsaturated alkylaminocarbonyl of the formula R$^5$-NH-C(O) wherein R$^5$ is a branched unsaturated hydrocarbon radical such as 1-methyl-1-(2-propenyl)-3-butenyl. Note, however, that when the requisite isocyanate intermediates are applied according to the procedure of example 7, then the ultimate product will be the corresponding peptide of formula 1 in which the N-terminus is saturated. Moreover, the latter procedure represents a practical process for preparing such corresponding peptides; for example, MePr$_2$CNHC(O)— or EtPr$_2$-CNHC(O)-Tbg-CH$_2$-(R)-CH(CH$_2$C(O)CMe$_3$)C(O)-Asp(cyPn)-NHCH$_2$CMe$_3$, see the 8th and the 10th compounds listed in Table VI of example 20, respectively.

On the other hand, when it is desired to retain the unsaturation at the N-terminus, the N-terminal unsaturated peptides of formula 1 can be prepared in the same manner as for the corresponding saturated peptides provided that one employs carboxy protective groups which can be selectively removed in the presence of the unsaturation. A practical carboxy protective group for this purpose is the allyl group. Accordingly, the desired N-terminus unsaturated peptides can be prepared by following the procedure of examples 2 to 4 and 7 but replacing (S)-α-azido-1-{(phenylmethoxy}carbonyl cyclopentanoic acid of example 2 with (S)-α-azido-1-(2-propenyloxycarbonyl)cyclopentanoic acid. The latter compound has been prepared in exactly the same manner as described for the phenylmethoxy derivative in example 2(a) except that benzyl bromide was replaced with allyl bromide. The final deprotection step (i.e. the removal of the carboxy protective group, or groups in the instance wherein E of the target peptide is NHCH(R$^{12}$)-Z wherein R$^{12}$ is as defined herein and Z is C(O)OH, can be accomplished accordingly to the procedure of R. Déziel, Tetrahedron Lett., 28, 4371 (1987), preferably with pyrrolidine in the presence of tetrakis(triphenylphosphine) palladium(O). An example of an N-terminal unsaturated peptide of formula 1 thus prepared is Me(CH$_2$=CH-CH$_2$)$_2$CNHC(O)-Tbg-CH$_2$-(R)-CH(CH$_2$C(O)CMe$_3$)C(O)-Asp(cyPn)-NHCH$_2$CMe$_3$, see the 7th compound listed in Table VI of example 20.

Note also that when E of the target N-terminal unsaturated peptide represents NHCH(R$^{10}$)-Z wherein R$^{10}$ is as defined herein and Z is CH$_2$OH, the intermediate used to incorporate the hydroxy bearing C-terminus unit into the desired peptide requires protection for the nascent C-terminal hydroxyl. The hydroxy protective group in this instance should also be one which can be selectively removed in the presence of the unsaturation. A convenient protective group in this instance is the allyoxy-carbonyl group, see E. J. Corey and J. W. Suggs, J. Org. Chem., 38 3223 (1973).

Some examples of other compound of formula 1 that can be prepared thus are (PhCH$_2$)$_2$CHC(O)-(N-Me)Val-Tbg-CH$_2$-(R)-CH(CH$_2$C(O)CMe$_3$)C(O)-Asp(cypn)-NHCH$_2$CMe$_3$ and (PhCH$_2$)$_2$CHC(O)-(N-Me)Val-Tbg-CH$_2$-(R)-CH(CH$_2$C(O)CMe$_3$)C(O)-Asp(cyPn)-NH-(R)-CH(Me)CMe$_3$.

EXAMPLE 10

Preparation of the Intermediate H-Asp(cypn) (Bzl)-NH-(R)-CH(Et)CMe$_3$ (the compound of formula 13 wherein R$^4$ is NH$_2$ and W$^3$ is Bzl)

By following the coupling procedure of example 1 and using the hydrogen chloride salt of NH$_2$-(R)-CH(Et)CMe$_3$ of example 9 as the first reactant and (S)-α-azido-1-{(phenylmethoxy)-carbonyl}cyclopentaneacetic acid of section (a) of this example as the second reactant, N-{1(R)-ethyl-(2,2-dimethylpropyl)}-(S)-α-azido-1-{(phenylmethoxy)carbonyl}cyclopentaneacetamide was obtained. Reduction of the latter compound with tin(II) chloride in MeOH according to the method of N. Maiti et al., Tetrahedron Letters, 27, 1423 (1986), followed by purification by chromatography (SiO$_2$, hexane —Et$_2$O, 1:1), gave the title compound of this example. $^1$H NMR (CDCl$_3$) δ7.36–7.27 (m, 5H), 7.08 (d, J=10.5 Hz, 1H), 5.17 (d, J=12.3 Hz, 1H), 5.09 (d, J=12.3 Hz, 1H), 3.72 (s, 1H), 3.56 (ddd, J=10.5, 10.5, 2.5 Hz, 1H), 2.23–1.15 (m, 2H), 1.87–1.80 (m, 1H), 1.76–1.57 (m, 8H), 1.17–1.03 (m, 1H), 0.88 (s, 9H) and 0.86 (t, J=7.3 Hz, 3H) .

EXAMPLE 11

Preparation of the Intermediate Boc-Tbg-CH$_2$-(R)-CH(CH$_2$C(O)CMe$_3$)C(O)OBzl (the compound of formula 2 wherein W$^1$ is Boc and W$^2$ is Bzl)

(a) Boc-Tbg-OMe (the compound of formula 3 wherein W$^1$ is Boc): A solution of Boc-Tbg-OH (68 g, 0.30 mol) in dry CH$_3$CN (0.5 L) was cooled to 0°. 1,8-Diazabicyclo [5.4.0]undec-7-ene (54 mL, 0.36 mol) was added over a period of 10 min to the cooled solution, followed by the addition of CH$_3$I (37 mL, 0.60 mol). The reaction mixture was stirred at room temperature (20°–22°) for 4 h and then concentrated under reduced pressure. The residue was partitioned between EtOAc and H$_2$O. The organic phase was washed with H$_2$O, an aqueous saturated solution of NaHCO$_3$ (2 X), and brine. Thereafter, the organic phase was dried (MgSO$_4$) and concentrated to afford a clear viscous liquid. This material was distilled bulb to bulb (oil pump vacuum, air bath temperature at 110°) to provide the desired product as a colorless oil (65 g, 88% yield). $^1$H NMR (CDCl$_3$) δ5.10 (broad d, J=9.0 Hz, 1H), 4.10 (d, J 9.0 Hz, 1H), 3.72 (s, 3H), 1.44 (s, 9H), 0.96 (s, 9H).

(b) Boc-Tbg-CH$_2$-P(O)(OMe)$_2$ (the compound of formula 5 wherein W$^1$ is Boc): At −78° under a nitrogen atmosphere, a 5 L flask equipped with a mechanical stirrer, an addition funnel with jacket and a thermometer was charged with a solution of BuLi in hexane (3.60 mol, 361 mL of a 10N solution). A cold (−78°) solution of freshly distilled dimethyl methylphosphonate (391 mL, 3.60 mol) in dry THF (1 L) was added dropwise via the addition funnel over a 1 h period. The mixture was stirred at −78° for 30 min. A cold (−78°) solution of Boc-Tbg-OMe (111 g, 0.452 mol) in THF (0.5 L) was added dropwise over a 20 min period. The reaction was stirred at −78° for 45 min, and then allowed to warm to about −30° over a 30 min period. Following the sequential addition of glacial acetic acid (0.25 L) and H$_2$O (0.3 L), the mixture was extracted with EtOAc (1 L). The organic layer was washed with H$_2$O, a 10% aqueous solution of NaHCO$_3$ and brine, dried (MgSO$_4$) and concentrated. The resulting solid was triturated with hexane to give the desired phosphonate as a white powder with mp 84°–86° (144 g, 95% yield). $^1$H NMR (CDCl$_3$) δ5.23 (broad d, J=9.0 Hz, 1H), 4.25 (d, J=9.0 Hz, 1H), 3.80 (d, J=11.4 Hz, 6H), 3.30 (dd, J=22.0, 14.6 Hz, 1H), 3.12 (dd, J=22.0, 14.6 Hz, 1H), 1.44 (s, 9H), 1.00 (s, 9H).

The phosphonate is used in section (d) of this example.

(c) HC(O)C(O)OBzl (the compound of formula 6 wherein W$^2$ is Bzl): Solid H$_5$IO$_6$ (49.3 g, 0.216 mol) was added portionwise to a solution of dibenzyl L-tartrate (70 g, 0.21 mol) in Et$_2$O (900 mL). The mixture was stirred for 2.5 h at room temperature and then filtered. The filtrate was dried (MgSO$_4$) and concentrated. The residual syrup was dissolved in hexane-Et$_2$O (2:3). The resulting milky solution was filtered through a pad of diatomaceous earth. The pad was washed with hexane-Et$_2$O (2:5). The combined filtrate and washing were concentrated to yield benzylglyoxylate as an oil (69.9 g, ~90% yield). H$^1$ NMR (CDCl$_3$) showed a mixture of aldehyde and hydrate form. Characteristic chemical shifts: δ9.25 (s), 7.87–7.21 (m, 5H), 5.47–5.03 (m), 4.56 (broad s).

(d) The γ-keto-α,β-unsaturated ester Boc-Tbg-(E)-CH=CHC(O)OBzl (the compound of formula 7 wherein $W^1$ is Boc and $W^2$ is Bzl): A solution of Boc-Tbg-CH$_2$-P(O)(OMe)$_2$ (121 g, 0.359 mol), described in section (b) of this example, and triethylamine (0.10 L, 0.72 mol) in CH$_3$CN (0.7 L) was stirred under nitrogen for 10 min at room temperature. Thereafter, a solution of HC(O)C(O)OBzl (121 g, ~0.36 mol) in CH$_3$CN (0.15 L) was added over 30 min. The mixture was stirred for 24 h and then concentrated. The residue was dissolved in Et$_2$O-hexane (2:1, 0.8 L). The solution was washed with a 10% aqueous solution of citric acid, a saturated solution of NaHCO$_3$ and brine, dried (MgSO$_4$) and concentrated. The resulting orange oil was passed through a silica gel pad (12×10 cm) using EtOAc-hexane (3:20) as the eluent. Concentration of the eluate gave the desired γ-keto-α,β-unsaturated ester as a yellow oil (112 g, 83% yield). $^1$H NMR (CDCl$_3$) δ7.42–7.32 (m, 5H), 7.23 (d, J=15.9 Hz, 1H), 6.80 (d, J=15.9 Hz, 1H), 5.25 (s, 2H), 5.21 (broad d, J=8.9 Hz, 1H), 4.43 (d, J=8.9 Hz, 1H), 1.42 (s, 9H), 0.96 (s, 9H).

The γ-keto-α,β-unsaturated ester is used in section (f) of this example.

(e) CH$_2$=CHCH$_2$OC(O)CH$_2$C(O)CMe$_3$ (the compound of formula 8): A solution of lithium bis(trimethylsilyl)amide in THF (1N, 0.8 L) was cooled to −78°. A solution of allyl acetate (39 mL, 0.36 mol) in THF (40 mL) was added dropwise to the cooled solution. The mixture was stirred at −78° for 1 h. Thereafter, a solution of trimethylacetyl chloride (47 mL, 0.38 mol) was added dropwise and the resulting mixture was stirred for 25 min at −78°. Hexane (0.3 L) and an aqueous solution of HCl (3N, 0.6 L) were added to the mixture. The organic phase was separated and washed with a saturated aqueous solution of sodium bicarbonate, brine and water. The organic phase was dried (MgSO$_4$), and concentrated to afford an orange oil. Distillation (bulb to bulb, air bath temperature of 60°, 0.25 Tor.) of the crude product gave desired ester as a colorless oil (62 g, 92% yield). $^1$H NR (CDCl$_3$) δ6.02–5.87 (m, 1H), 5.35 (broad d, J=17.2 Hz, 1H), 5.25 (broad d, J=9.5 Hz, 1H), 4.63 (broad d, J=5.6 Hz, 2H), 3.59 (s, 2H), 1.19 (s, 9H).

(f) The Michael adduct, i.e. Boc-Tbg-CH$_2$-(R)-CH{CH(C(O)CMe$_3$)(C(O)OCH$_2$CH=CH$_2$)}C(O)OBzl (the compound of formula 9 wherein $W^1$ is Boc and $W^2$ is Bzl): Solid NaH (2.7 g of a 60% oil dispersion, 0.07 mol) was added over a 15 min period to a solution of CH$_2$=CHCH$_2$OC(O)CH$_2$C(O)CMe$_3$ (83.2 g, 0.452 mol) in THF (0.8 L). The reaction mixture was stirred at room temperature under an atmosphere of argon until all the solid dissolved (30 min). The homogeneous solution was cooled to −60° (solution temperature) and a solution of Boc-Tbg-(E)-CH=CHC(O)OBzl (170 g, 0.45 mol), described in section (d) of this example, in THF (0.5 L) was added slowly over a period of 45 min. Thereafter, the reaction mixture was stirred at −60° for 5 h. A 10% aqueous solution of citric acid was added and the mixture was allowed to warm to room temperature. The mixture was extracted with Et$_2$O. The organic phase was washed with a 5% aqueous solution of sodium bicarbonate and brine, dried (MgSO$_4$) and concentrated to afford an orange oil (250 g) which was used without further purification in the next reaction.

(g) Boc-Tbg-CH$_2$-(R)-CH(CH$_2$C(O)CMe$_3$)C(O)-OBzl: Pyrrolidine (56 mL, 0.54 mol) was added to a stirred solution of tetrakistriphenylphosphine palladium(O) (2.60 g, 2.25 mmol, 0.5% molar) in CH$_2$Cl$_2$ (250 mL) and CH$_3$CN (250 mL) at 0° under an atmosphere of argon. The mixture was allowed to warm to room temperature. A solution of the Michael adduct from the preceding section (250 g, 0.45 mol) in CH$_2$Cl$_2$-CH$_3$CN (200 mL:200 mL) was added to the mixture. After 3 h, the mixture was concentrated to yield an orange oil. The crude oil was dissolved in a mixture of Et$_2$O-hexane (1:1, 1 L). The solution was washed with a 10% aqueous solution of citric acid, 10% aqueous solution of sodium bicarbonate, and brine, dried (MgSO$_4$) and concentrated to give the title compound of this example as an orange oil (203 g, >90% yield). This material was used without further purification in example 5. A small sample was purified by SiO$_2$ chromatography. Elution with hexane-EtOAc (9:1) gave the pure title compound as a colorless oil. $[\alpha]_D^{25}$+11.5 (c=1.3, CHCl$_3$); $^1$H NMR (CDCl$_3$) δ7.38–7.28 (m, 5H), 5.10 (s, 2H), 5.07 (broad d, J=9.2 Hz, 1H), 4.08 (d, J=9.2 Hz, 1H), 3.38–3.31 (m, 1H), 3.09 (dd, J=18.8, 6.0 Hz, 1H), 2.94 (dd, J=18.4 6.1 Hz, 1H), 2.82 (dd, J=18.4, 6.1 Hz, 1H), 2.77 (dd, J=18.8, 6.0 Hz, 1H), 1.42 (s, 9H), 1.10 (s, 9H), 0.95 (s, 9H). The diastereoisomeric purity was assessed to be >35:1 by NMR; see P. L. Beaulieu et al., European patent application 560 267, published Sep. 15, 1993. In order to assess the enantiomeric purity of the title compound, the Boc protective group ($W^1$) was removed with 4N HCl in dioxane and the resulting amine was converted to a Mosher amide (see J. A. Dale et al., vide supra). By comparing results from a product prepared by the procedure of this example with results obtained with a racemic mixture of the title compound, the enantiomeric excess for said product was determined to be >96% by NMR and >99% by chiral column chromatography. The latter determination was performed by normal phase HPLC on a Chiracel® OD column from Daicel Chemical Industries Limited, Tokyo, Japan (US distributor: Chiral Technologies Inc., Exton Pa., USA). EtOH-hexane (1:19) was the eluent and UV detection at 215 nm was employed.

EXAMPLE 12

Preparation of the Intermediate Boc-Tbg-CH$_2$-(R)-CH(CH$_2$C(O)CMe$_3$)C(O)OH (the compound of formula 14 wherein $W^1$ is Boc)

To a solution of the title compound of example 11 (171 g, 0.36 mol) in EtOH (1.4 L) was added 10% Pd/C (10 g). The resultant mixture was stirred vigorously under one atmosphere of hydrogen for 5 h. Thereafter, the reaction mixture was subjected to filtration through diatomaceous earth. The filtrate was concentrated under reduced pressure. The residue was dissolved in a saturated aqueous solution of Na$_2$CO$_3$. The aqueous solution was washed with hexane-Et$_2$O (8:2), rendered acidic with citric acid and extracted with EtOAc. The extract was dried (MgSO$_4$) and concentrated. The orange residue was dissolved in Et$_2$O and the resulting solution was passed through a silica gel pad (12×12 cm). Concentration gave the title compound of this example as a solid with mp 62°65° (117 g, 84% yield). $^1$H NMR (CDCl$_3$) δ5.18 (d, J=8.8 Hz, 1H), 4.09 (d, J=8.8 Hz, 1H), 3.35–3.29 (m, 1H), 3.09 (dd, J=18.8, 6.3 Hz), 2.94 (dd, J=18.4, 6.3 Hz, 1H), 2.83 (dd, J=18.4, 6.3 Hz, 1H), 2.78 (dd, 18.8, 6.3 Hz, 1H), 1.43 (s, 9H), 1.14 (s, 9H) , 0.96 (s, 9H).

EXAMPLE 13

Preparation of the Intermediate Boc-Tbg-CH$_2$-(R)-CH(CH$_2$C(O)CMe$_3$)C(O)-Asp(cyPn)(Bzl)-NH-(R)-CH(Et)CMe$_3$ (the compound of formula 15 wherein $R^5$ is Boc and $W^3$ is Bzl)

By following the coupling procedure of example 1 and using the title compound of example 10 as the first reactant and the title compound of example 12 as the second reactant, the title compound of this example is obtained: $^1$H NMR (CDCl$_3$) δ7.43–7.26 (m, 6H), 6.76 (d, J=10.0 Hz, 1H), 5.16

(s, 2H), 5.06 (d, J=8.9 Hz, 1H), 4.62 (d, J=8.9 Hz, 1H), 4.07 (d, J=8.9 Hz, 1H), 3.60 (ddd, J=10.0, 10.0, 2.5 Hz, 1H), 3.18–2.83 (m, 3H), 2.70 (dd, J=16.9, 4.1 Hz, 1H), 2.68–2.54 (m, 1H), 1.90–1.52 (m, 9H), 1.42 (s, 9H), 1.11 (s, 9H), 0.94 (s, 9H), 0.88 (s, 9H), 0.78 (t, J=7.3 Hz, 3H).

EXAMPLE 14

Preparation of $(1\alpha,2\alpha,6\alpha)$-2,6-dimethyl-1-isocyanatocyclohexane (the compound of formula 17 wherein $R^1$ and $R^3$ is methyl and $R^2$ is hydrogen)

$(1\alpha,2\alpha,6\alpha)$-2,6-dimethyl-1-cyclohexanamine hydrochloride was prepared as follows: 2,6-Dimethylphenol was subjected to hydrogenation in the presence of Rh-Al$_2$O$_3$, followed by oxidation of the resulting 2,6-dimethylcyclohexanol isomers with chromic acid according to the method of I. J. Borowitz et al., J. Org. Chem., 37, 581 (1972) to obtain a mixture of cis and trans isomers of 2,6-dimethylcyclohexanone. The latter isomeric mixture of ketones was converted to a corresponding mixture of oximes, which was separated by chromatography on SiO$_2$. The desired cis isomer of 2,6-dimethylcyclohexanone oxime was reduced (platinum black, 50 psi of hydrogen in a Parr hydrogenator glacial acetic acid, hydrochloric acid, 14 h) to give the desired $(1\alpha,2\alpha,6\alpha)$-2,6-dimethyl-1-cyclohexanamine as its hydrochloric acid addition salt, mp >280° C. The method for preparing and reducing the oximes to amines has been described previously by G. Bellucci et al., Gazz. Chim. Ital., 99, 1217 (1969).

The latter hydrochloric acid addition salt (3.11 g, 19.0 mmol) was suspended in toluene (100 mL) and a solution of phosgene in toluene (1.93M, 4.9 mL, 95 mmol) was added. The mixture was heated at reflux for 2 h and then concentrated under reduced pressure to give the title compound as a clear colorless oil. This material was used as such in the following example.

In the same manner, other requisite substituted isocyanatocyclohexanes can be prepared. For example, $(1\alpha,2\alpha,6\alpha)$-2,6-diethyl-1-isocyanatocyclohexane was prepared from 2,6-diethylphenol via $(1\alpha,2\alpha,6\alpha)$-2,6-diethyl-1-cyclohexanamine hydrochloride, mp >280°, and $(1\alpha,2\alpha,4\alpha,6\alpha)$-2,4,6-trimethyl-1-isocyanatocyclohexane was prepared from 2,4,6-trimethyl phenol via $(1\alpha,2\alpha,4\alpha,6\alpha)$-2,4,6-trimethyl-1-cyclohexanamine hydrochloride, mp >280°.

EXAMPLE 15

Preparation of {{(1α,2α,6α)-2,6-Dimethyl-1-cyclohexanamino}carbonyl}-Tbg-CH$_2$-(R)-CH(CH$_2$C(O)CMe$_3$)C(O)-Asp(cyPn)-NH-(R)-CH(Et)CMe$_3$ (the compound of formula 1 wherein A and B together form an alkylaminocarbonyl of the formula Q' wherein $R^{1A}$ and $R^{3A}$ are methyl and $R^{2A}$ is hydrogen)

To a solution of the title compound of example 13 (11.17 g, 15.05 mmol) in CH$_2$Cl$_2$ (20 mL) was added 4M HCl/dioxane (100 mL). The mixture was stirred at room temperature for 30 min and then concentrated under reduced pressure to give H-Tbg-CH$_2$-(R)-CH(CH$_2$C(O)CMe$_3$)C(O)-Asp(cyPn)(Bzl)-NH-(R)-CH(Et)CMe$_3$ in the form of its hydrochloric acid addition salt. A suspension of the latter salt in dry CH$_2$Cl$_2$ (100 mL) was cooled to 0°. A solution of $(1\alpha,2\alpha,6\alpha)$-2,6-dimethyl-1-iso-cyanatocyclohexane (~19 mmol), prepared as described in example 14, in dry CH$_2$Cl$_2$ (25 mL) was added to the cooled suspension. The mixture was stirred at 0° for 5 min. N-Methylmorpholine (3.3 mL, 30 mmol) was added to the mixture. Thereafter, the mixture was stirred at room temperature for 16 h and then concentrated under reduced pressure. The resulting residue was partitioned between EtOAc and a 5% aqueous solution of Na$_2$CO$_3$. The organic phase was washed with 1N aqueous HCl and brine, dried (MgSO$_4$) and concentrated under reduced pressure. The resulting crude product was purified by flash chromatography (SiO$_2$, eluent:EtOAc/hexane, 1.5–2.5:10) to provide the corresponding benzyl ester of the title compound as a foam (9.59 g, 90% yield, after being dried to constant weight in high vacuum). This product was used as such for the following hydrogenolysis reaction.

The latter benzyl ester (9.59 g, 13.6 mmol) was subjected to hydrogenolysis (10% Pd/C (1.0 g), 1 atmosphere of H$_2$, absolute EtOH (150 mL), 2.5 h). The reaction mixture was filtered through a glass microfiber filter. The filtrate was concentrated under reduced pressure to ⅓ of its initial volume. This concentrate was filtered through a 0.4 µm membrane. The resulting filtrate was concentrated and the residue was crystallized (2 X) from EtOH-water to give the title compound as a white solid that was dried at 98° under high vacuum for 48 h (6.95 g, 85% yield). Mp 158°–160°; $^1$H NMR (d$_6$-DMSO) δ8.24 (d, J=10 Hz, 1H), 6.93 (d, J=10 Hz, 1H), 6.32 (d, J=8.5Hz, 1H), 5.82 (d, J=10 Hz, 1H), 4.93 (d, J=10 Hz, 1H), 4.00 (d, J=8.5 Hz, 1H), 3.67–3.63 (m, 1H), 3.45–3.37 (m, 1H), 3.23–3.15 (m, 1H), 2.78–2.59 (m, 4H), 2.08–2.01 (m, 1H), 1.70–1.47 (m, 13H), 1.34–1.19 (m, 4H), 1.03 (s, 9H), 0.93 (s, 9H), 0.87 (s, 9H), 0.74 (d, J=6.5 Hz, 3H), 0.72 (d, J=6.5 Hz, 3H), 0.64 (t, J=7 Hz, 3H), FAB MS (m/z):705.4 (M+H)$^+$; Anal.: calculated for C$_{39}$H$_{68}$N$_4$O$_7$: C, 66.54; H, 10.01; N, 7.79; found, C, 66.18; H, 9.96; N, 7.88.

By following the procedure of this example but replacing $(1\alpha,2\alpha,6\alpha)$-2,6-dimethyl-1-isocyanatocyclohexane with $(1\alpha,2\alpha,6\alpha)$-2,6-diethyl-1-isocyanatocyclohexane, then {{ (1α,2α,6α)-2,6-diethyl-1-cyclo-hexanamino}carbonyl}-Tbg-CH$_2$-(R)-CH(CH$_2$C(O)CMe$_3$)-C(O)-Asp(cyPn)-NH-(R)-CH(Et)CMe$_3$ was obtained: FAB/MS (m/z): 733.7 (M+H)$^+$.

By following the procedure of this example but replacing $(1\alpha,2\alpha,6\alpha)$-2,6-dimethyl-1-isocyanatocyclohexane with an equivalent amount of $(1\alpha,2\alpha,4\alpha,6\alpha)$-2,4,6-trimethyl-1-isocyanato-cyclohexane, then {{(1α,2α,4α,6α)-2,4,6-trimethyl-1-cyclohexanamino}carbonyl}-Tbg-CH$_2$-(R)-CH(CH$_2$C (O) CMe$_3$)C(O)-Asp(cyPn)-NH-(R)-CH(Et)CMe$_3$ was obtained; FAB/MS (m/z): 719.8 (M+H)$^+$.

Thus, by using the appropriate intermediates, the serial coupling and the deprotection procedures of examples 1 to 15 can be used to prepare other compounds of formula 1, such as those exemplified in the tables of the following examples. In some cases, precipitation of the final product does not afford pure material. In those instances, the product can be purified by semi preparative HPLC on a C-18 reversed-phase column using a gradient of acetonitrile and water, each containing 0.06% TFA. To this end, the crude product was dissolved in 0.1M aqueous NH$_4$OH and the pH of the solution was brought back to about 7 using 0.1M aqueous AcOH, prior to purification. When applicable, diastereoisomeric mixtures were separated in this fashion.

EXAMPLE 16

Inhibition of Herpes Simplex Virus (HSV-1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et al., J. Gen.
Virol., 66, 733 (1985).

b) Assay The assay described by P. Gaudreau et al., J. Biol, Chem., 262, 12413 (1987),is used to evaluate the capability of the compounds of formula 1 to inhibit HSV-1 ribonucleotide reductase activity. The assay results are expressed as the concentration of the compound producing 50% of the maximal inhibition ($IC_{50}$) of enzyme activity. The number of units of the enzyme preparation used in each assay was constant, based on the specific activity of the enzyme preparation. The results are relative to the activity obtained in control experiments without the test compound and represent the means of four assays that varied less than 10% with each other.

The following TABLE I illustrates the assay results obtained for exemplified compounds of formula 1.

TABLE I

| Compound of Formula 1 | FAB/MS (m/z) (M + Na)+ | $IC_{50}$ μM |
|---|---|---|
| Title Compound of Example 6 | 813* | 0.27 |
| PhCH₂CH₂C(O)—(N—Me)Val—Tbg—CH₂—(R)—CH(CH₂C(O)CMe₃)C(O)—Asp(cyPn)—γMeLeu—OH | 849 | 0.19 |
| PhCH₂CH₂C(O)—(N—Me)Val—Tbg—CH₂—(R)—CH(CH₂C(O)CMe₃)C(O)—Asp(cyPn)—γMeLeu—NH₂ | 848 | 0.26 |
| PhCH₂CH₂C(O)—(N—Me)Val—Tbg—CH₂—(R)—CH(CH₂C(O)CMe₃)C(O)—Asp(cyPn)—NHCH₂CMe₃ | 791 | 0.33 |
| PhCH₂CH₂C(O)—(N—Me)Val—Tbg—CH₂—(R)—CH{CH₂C(O)—(cyclopentyl)}C(O)—Asp—(cyPn)—NHCH₂CMe₃ | 803 | 0.32 |
| PhCH₂CH₂C(O)—(N—Me)Val—Tbg—CH₂—(R)—CH(CH₂C(O)CMe₃)C(O)—Asp{(R)—Me}—NHCH₂CMe₃ | 751.5 | 0.33 |
| Et₂CHNHC(O)—Tbg—CH₂—(R)—CH(CH₂C(O)CMe₃)C(O)—Asp(cyPn)—NHCH₂CMe₃ | 659 | 0.23 |
| Et₂CHNHC(O)—Tbg—CH₂—(S)—CH{CH₂C(O)(pyrrolidino)}C(O)—Asp (cyPn)—γMeLeucinol | 716 | 0.17 |
| Et₂CHNHC(O)—Tbg—CH₂—(R)—CH(CH₂C(O)CMe₃)C(O)—Asp (cyPn)—γMeLeu—OH | 717 | 0.12 |
| Et₂CHNHC(O)—Tbg—CH₂—(R)—CH(CH₂C(O)CMe₃)C(O)—Asp(cyPn)γMeLeu—NH₂ | 716 | 0.22 |
| Title Compound of Example 7 | 703 | 0.15 |
| Et₂CHNHC(O)—Tbg—CH₂—(R)—CH{CH₂C(O)—(cyclopentyl))C(O)—Asp(cyPn)—NHCH₂CMe₃ | 671 | 0.22 |
| Et₂CHNHC(O)—Tbg—CH₂—(R)—CH(CH₂C(O)CMe₃)C(O)—Asp{(R)—Me}—NHCH₂CMe₃ | 597* | 0.20 |
| Pr₂CHNHC(O)—Tbg—CH₂—(R)—CH(CH₂C(O)CMe₃)C(O)—Asp(cyPn)—γMeLeu—OH | 745 | 0.15 |
| Pr₂CHNHC(O)—Tbg—CH₂—(R)—CH(CH₂C(O)CMe₃)C(O)—Asp(cyPn)—γMeLeucinol | 731 | 0.20 |
| Pr₂CHNHC(O)—Tbg—CH₂—(R)—CH(CH₂C(O)CMe₃)C(O)—Asp(cyPn)—NHCH₂CMe₃ | 665* | 0.08 |
| {{(1α,2α,6α)-2,6-dimethyl-1-cyclohexanamino}carbonyl}—Tbg—CH₂—(CH₂C(O)—CMe₃)C(O)—Asp(cyPn)(Bzl)—NH—(R)—CH(Et)CMe₃ | 705.4* | 0.095 |
| {{(1α,2α,6α)-2,6-diethyl-1-cyclohexanamino}carbonyl}—Tbg—CH₂—(CH₂C(O)—CMe₃)C(O)—Asp(cyPn)(Bzl)—NH—(R)—CH(Et)CMe₃ | 733.7* | 0.110 |
| {{(1α,2α,4α,6α)-2,4,6-trimethyl-1-cyclohexanamino)carbonyl)—Tbg—CH₂—(CH₂C(O)—CMe₃)C(O)—Asp(cyPn)(Bzl)—NH—(R)—CH(Et)CMe₃ | 719.8* | 0.130 |

*(M + H)+

EXAMPLE 17

Inhibition of Herpes Simplex Virus (HSV-2) Replication in Cell Culture

Assay:

BHK-21/C13 cells (ATCC CCL 10) are incubated for two days in 150 cm² T-flasks (1.5×10⁶ cells/flask) with alpha-MEM medium (Gibco Canada Inc., Burlington, Ontario, Canada) supplemented with 8% (v/v) fetal bovine serum (FBS, Gibco Canada Inc.). The cells are trypsinized and then transferred to fresh media in a 24 well plate to give 2.5×10⁵ cells in 750 μL of media per well. The cells are incubated at 37° for a period of 6 h to allow them to adhere to the plate. Thereafter, the cells are washed once with 500 μL of alpha-MEM supplemented with 0.5% (v/v) FBS and then incubated with 750 μL of the same media (low serum) for 3 days. After this period of serum starvation, the low serum medium is removed and the cells are incubated in 500 μL of BBMT for 2 to 3 h. {BBMT medium is described by P. Brazeau et al., Proc. Natl. Acad. Sci. USA, 79, 7909 (1982).} Thereafter, the cells are infected with HSV-2 (multiplicity of infection =0.02 PFU/cell) in 100 μL of BBMT medium. (Note: The HSV-2 used was strain HG-52, see Y. Langelier and G. Buttin, J. Gen. Virol., 57, 21 (1981); the virus was stored at −80°.) Following 1 h of virus adsorption at 37°, the media is removed and the cells are washed with BBMT (3×250 μL). The cells in each well are incubated with or without 200 μL of appropriate concentrations of the test agent in BBMT medium. After 28 h of incubation at 37°, the infected cells are harvested by first freezing the plate at −80°, followed by thawing. The cells in each well are scraped off the surface of the well with the help of the melting ice fragments. After complete thawing, the cell suspensions are collected and each well is rinsed with 150 μL of BBMT medium. The viral sample (suspension plus washing) is sonicated gently for 4 min at 4°. Cell debris are removed by centrifugation (1000 times gravity for 10 min at 4°). The supernatant is collected and stored at −80° until determination of viral titer.

Viral titration was performed by a modification of the colorimetric assay method of M. Langlois et al., Journal of Biological Standardization, 14, 201 (1986), and the application of the modified method to this cell culture assay is described in detail by R. Déziel and Y. Guindon, vide supra.

Accordingly, the percentage of virus growth inhibition can be determined for the various concentrations of the test agent. From this data, the $EC_{50}$, i.e. the concentration of the test agent effecting a 50% inhibition of virus replication, can be calculated.

Results:

The following Table II provides examples of the results obtained when compounds of formula 1 were evaluated according to the cell culture assay of this example.

TABLE II

| Compound of Formula 1 | $EC_{50}$ μM |
|---|---|
| Title Compound of Example 6 | 15 |
| PhCH₂CH₂C(O)—(N—Me)Val—Tbg—CH—(R)—CH(CH₂C(O)CMe₃)C(O)—Asp(cyPn)—γMeLeu—OH | 65 |
| PhCH₂CH₂C(O)—(N—Me)Val—Tbg—CH—(R)—CH(CH₂C(O)CMe₃)C(O)—Asp(cyPn)—γMeLeu—NH₂ | 60 |
| Et₂CHNHC(O)—Tbg—CH₂—(R)—CH(CH₂C(O)CMe₃)C(O)—Asp(cyPn)—NHCH₂CMe₃ | 56 |
| Et₂CHNHC(O)—Tbg—CH₂—(S)—CH{CH₂C(O)(pyrrolidino)}C(O)—Asp (cyPn)—γMeLeucinol | 200 |
| Et₂CHNHC(O)—Tbg—CH₂—(R)—CH{CH₂C(O)(cyclopentyl)}C(O)—Asp(cyPn)—NHCH₂CMe₃ | 50 |
| Pr₂CHNHC(O)—Tbg—CH₂—(R)—CH(CH₂C(O)CMe₃)C(O)—Asp (cyPn)—γMeLeucinol | 30 |

TABLE II-continued

| Compound of Formula 1 | $EC_{50}$ $\mu M$ |
|---|---|
| $Pr_2CHNHC(O)$—Tbg—$CH_2$—(R)—$CH(CH_2C(O)$—$CMe_3)C(O)$—Asp(cyPn)—$NHCH_2CMe_3$ | 24 |
| (1-propylcyclopentyl)aminocarbonyl-Tbg—$CH_2$—(R)—$CH(CH_2C(O)CMe_3)C(O)$—Asp (cyPn)—$NHCH_2CMe_3$ | 40 |
| $Pr_2CHNHC(O)$—Tbg—$CH_2$—(R)—$CH\{CH_2C(O)$-(cyclopentyl)$\}C(O)$—Asp(cyPn)—$NHCH_2CMe_3$ | 30 |
| $\{\{(1\alpha,2\alpha,6\alpha)$-2,6-dimethyl-1-cyclohexanamino$\}$carbonyl$\}$—Tbg—$CH_2(CH_2C(O)$—$CMe_3)C(O)$—Asp(cyPn) (Bzl)—NH—(R)—$CH(Et)CMe_3$ | 7 |
| $\{\{(1\alpha,2\alpha,6\alpha)$-2,6-diethyl-1-cyclohexanamino$\}$carbonyl$\}$—Tbg—$CH_2$—$(CH_2C(O)$—$CMe_3)C(O)$—Asp(cyPn) (Bzl)—NH—(R)—CH $(Et)CMe_3$ | 5 |
| $\{\{(1\alpha,2\alpha,6\alpha)$-2,4,6-trimethyl-1-cyclohexanamino$\}$carbonyl$\}$—Tbg—$CH_2$—$(CH_2C(O)$—$CMe_3)C(O)$—Asp(cyPn) (Bzl)—NH—(R)—$CH(Et)CMe_3$ | 6 |

EXAMPLE 18

Comparison of Acyclovir the Title Peptide of Formula 1 of Example 6 and the Combination of the Two Agents in Inhibiting HSV-2 Replication in Cell Culture The following Table III is illustrative of the results obtained when acyclovir and the title peptide of example 6 and combinations of the two were evaluated according to the assay procedure of example 17.

TABLE III

| COMPOUND | RANGE OF SAMPLE CONCENTRATIONS EVALUATED | $EC_{50}$ $\mu M$ |
|---|---|---|
| acyclovir* | 0.032 to 20 $\mu M$ | 3.5 |
| peptide** | 1.23 to 100 $\mu M$ | 19 |
| acyclovir + 2 $\mu M$ of peptide | 0.32 to 20 $\mu M$ | 1.4 |
| acyclovir + 4 $\mu M$ of peptide | 0.32 to 20 $\mu M$ | 0.9 |
| acyclovir + 6 $\mu M$ of peptide | 0.32 to 20 $\mu M$ | 0.9 |
| acyclovir + 8 $\mu M$ of peptide | 0.32 to 20 $\mu M$ | 0.8 |
| acyclovir + 10 $\mu M$ of peptide | 0.32 to 20 $\mu M$ | 0.42 |

*acyclovir was obtained from Burroughs Wellcome Inc., Kirkland, Quebec, Canada
**The title compound of formula 1 of example 6.

The results demonstrate a synergistic action between acyclovir and the compound of formula 1 in that the addition to the peptide to acyclovir affords combinations with $EC_{50}$'s significantly lower than the $EC_{50}$ of acyclovir alone.

The synergism of the combination of acyclovir and the compound of formula 1 can further be demonstrated by applying the isobole method to the above results, see J. S ühnel, Antiviral Research, 13, 23 (1990) and references therein. The positive result obtained in the application of this method is illustrated graphically in the accompanying FIG. 1.

EXAMPLE 19

Synergistic Combinations

The synergistic action between the title compound of example 15 and acyclovir (ACV) against HSV-1 and HSV-2 was demonstrated by evaluating the two agents, each alone and then in various combinations in the cell culture assay, using strains of HSV-1 or HSV-2 and applying the isobole method to the results obtained in these studies; see J. S ühnel, J. Antiviral Research, 13, 23 (1990).

More explicitly with reference to the isobole method, this method requires experimental data generated for the two test compounds, each alone and in different combinations. In this way selected concentrations of the title compound of example 15 ($EC_5$, $EC_{10}$, $EC_{20}$ and $EC_{30}$) were added to a given concentration of ACV and the ECSO's were evaluated as described previously. For these experiments, the $EC_5$, $EC_{10}$, $EC_{20}$ and $EC_{30}$ of the title compound of example 15 (i.e. the test compound) were derived from inhibition curves previously obtained. An isobologram is generated using a value termed $FIC_{60}$ (ACV) (which is the ratio of the concentration of ACV required to inhibit HSV replication by 60% in the presence of a fixed concentration of the test compound to the concentration required in the absence of the test compound). This is plotted against a term representing the ratio of the fixed concentration of the test compound to the concentration of the test compound that reduced 60% inhibition of HSV replication in the absence of ACV.

Equations:

$$X \text{ axis}: \frac{[\text{the fixed concentration of the test compound added}]}{EC_{60} \text{ of the test compound alone}}$$

$$Y \text{ axis}: FIC_{60}(ACV) = \frac{EC_{60}(ACV + X \mu M \text{ of the test compound})}{EC_{60}(ACV \text{ alone})}$$

The following TABLES IV and V are illustrative of results obtained when combinations of ACV and the title compound of example 15 (TC) were evaluated for their antiherpes activity against HSV-1 and HSV-2.

The virus strains and their multiplicity of infections (MOI) employed were HSV-1 KOS strain (MOI=0.01 PFU/cell) for the studies illustrated in TABLE IV, and HSV-2 HG-52 strain (MOI=0.02 PFU/cell) for the studies illustrated in TABLE V.

TABLE IV

SYNERGISTIC STUDIES OF ACYCLOVIR (ACV) AND THE TITLE COMPOUND OF EXAMPLE 15 (TC) AGAINST HSV-1

| COMPOUNDS | $EC_{50}$ $(\mu M)^1$ |
|---|---|
| Compound Alone | |
| ACV 2 | 2.2 |
| TC | 2.3 |
| Synergistic Studies | |
| ACV + 1.0 $\mu M$ of TC | 0.70 |
| ACV + 1.2 $\mu M$ of TC | 0.55 |
| ACV + 1.4 $\mu M$ of TC | 0.50 |
| ACV + 1.6 $\mu M$ of TC | 0.22 |
| ACV + 1.8 $\mu M$ of TC | 0.16 |
| ACV + 2.0 $\mu M$ of TC ($EC_{30}$) | 0.12 |

TABLE V

SYNERGISTIC STUDIES OF ACYCLOVIR (AC) AND
THE TITLE COMPOUND OF EXAMPLE 15 (TC) AGAINST HSV-2

| COMPOUNDS | $EC_{50}$ ($\mu M$)[1] |
|---|---|
| Compound Alone | |
| ACV [2] | 1.8 |
| TC | 5.2 |
| Synergistic studies | |
| ACV + 2 $\mu M$ of TC | 0.28 |
| ACV + 3 $\mu M$ of TC | 0.38 |
| ACV + 4 $\mu M$ of TC ($EC_{30}$) | 0.16 |

[1] Stock Solutions of the title compound of example 15 were filtered through a 0.22 $\mu M$ membrane and then the concentration of the compound in the filtered solution was determined by HPLC.
[2] Acyclovir was obtained from Burroughs Wellcome Inc., Kirkland, Quebec, Canada.

Note: In the preceding studies of TABLES IV and V, the inhibition of the HSV replication was observed at concentrations significantly below the cytotoxic levels for the test compounds as determined by the cytotoxicity assay of F. Denizot and R. Lang, J. Immunol. Methods, 89, 271 (1986).

The results of TABLES IV and V show that, on combining the title compound of example 15 with acyclovir, a proportional lowering of the $IC_{50}$ of acyclovir is effected as the ratio of the concentrations of the title compound of example 15 is increased. Hence, these synergistic studies demonstrate that the compounds of formula 1 are able to potentiate the antiherpes activity of acyclovir against HSV-1 and HSV-2.

Figure 2:
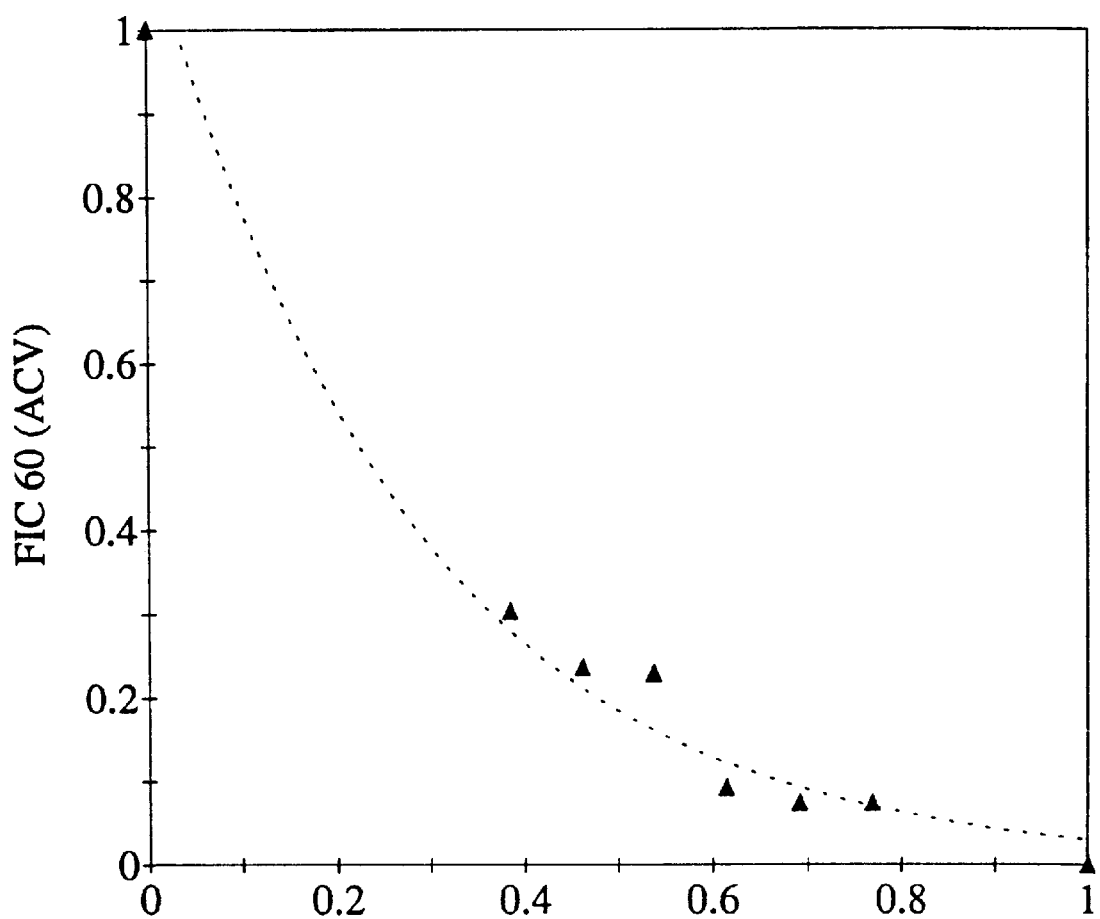
Figure 3:
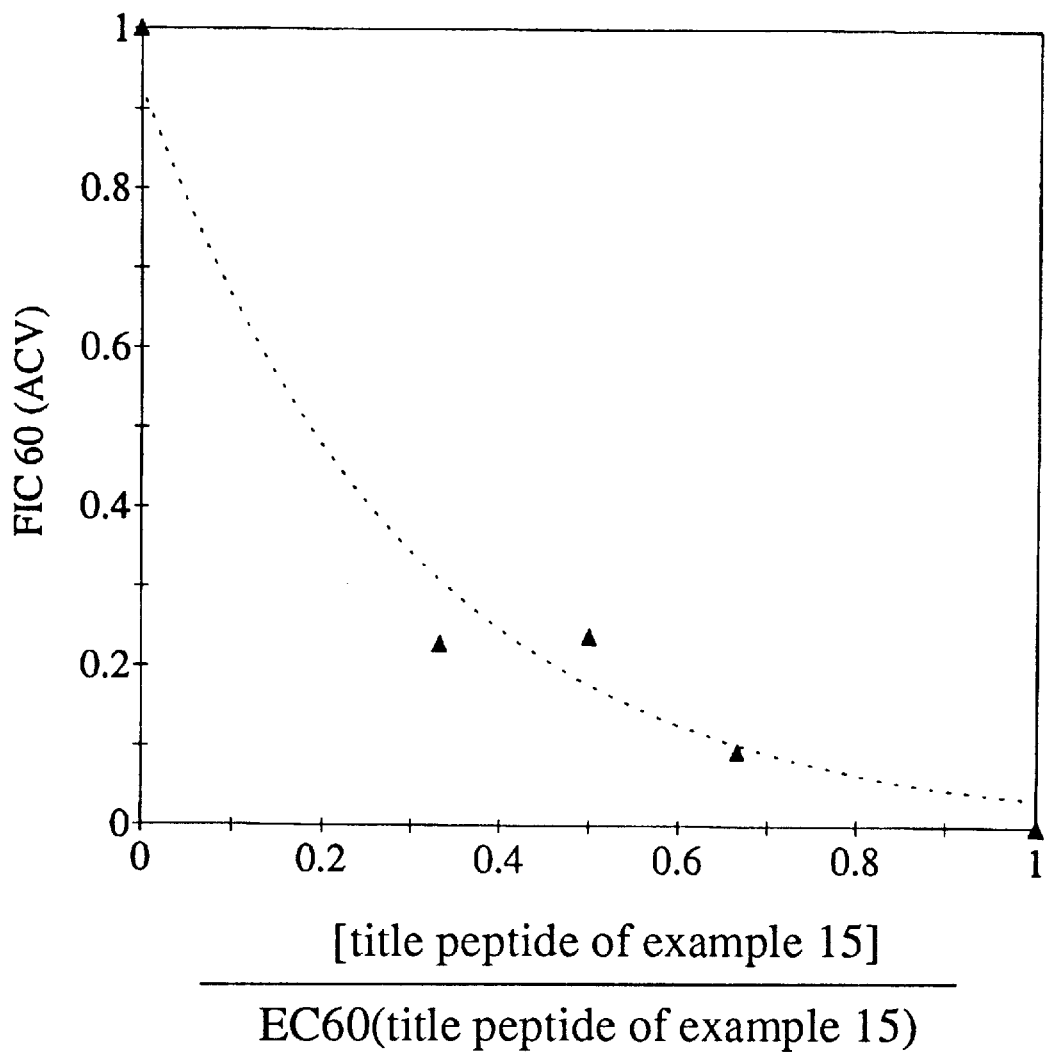

The results of TABLES IV and V are graphically illustrated in accompanying FIGS. 2 and FIGS. 3, respectively.

EXAMPLE 20

Still other examples of peptides of formula 1 of this application are included in the following Tables VI and VII together with characterizing mass spectra data and assay results in the assay of example 16, i.e. the $IC_{50}$; and the cell culture assay of example 17, i.e the $EC_{50}$.

TABLE VI

Compounds of Formula 1 having
the formula A—B—Tbg—$CH_2$—(R)—CH—
($CH_2C(O)CMe_3$)C(O)—Asp(cyPn)—E
wherein A—B and E are designated as follows:

| A—B | E | FAB/MS (m/z) (M+H)+ | $IC_{50}$ $\mu M$ | $EC_{50}$ $\mu M$ |
|---|---|---|---|---|
| $Pr_2$CHNHC(O) | NH—(R)—CH(Me)$CMe_3$ | 679 | 0.28 | 14 |
| $Pr_2$CHNHC(O) | NH$CH_2CMe_2$Et | 679 | 0.24 | 16 |
| $Pr_2$CHNHC(O) | NH$CH_2$—(R,S)—CH(Me)Et | 665 | 0.29 | 50 |
| $Pr_2$CHNHC(O) | NH$CH_2$CH$Et_2$ | 679 | 0.41 | 42 |
| Me$Pr_2$CNHC(O) | NH$CH_2CMe_2$Et | 693 | 0.36 | 29 |
| $Pr_2$CHNHC(O) | NHNH$CMe_3$ | 666 | 0.22 | 84 |
| Me($CH_2$=$CHCH_2$)$_2$—CNHC(O) | NH$CH_2CMe_3$ | 691 | 0.27 | 30 |
| Me$Pr_2$CNHC(O) | NH$CH_2CMe_3$ | 678 | 0.28 | 26 |
| $Pr_2$CHNHC(O) | NH$CH_2$-(cyclohexyl) | 691 | 0.36 | 47 |
| Et$Pr_2$CNHC(O) | NH$CH_2CMe_3$ | 693 | | 16 |
| ($CH_2$=$CHCH_2$)$_2$—CHNHC(O) | NH$CH_2CMe_3$ | 661 | 0.37 | 100 |
| $Bu_2$CHNHC(O) | NH$CH_2CMe_3$ | 693 | 0.53 | 65 |
| $Pr_2$CHNHC(O) | NH—(S)—CH($CMe_3$)$CH_2$OH | 695 | 0.23 | 48 |
| $Me_2$PrCNHC(O) | NH$CH_2CMe_3$ | 651 | 0.39 | 58 |
| $Pr_2$CHNHC(O) | NH$CH_2$C$Et_2$Me | 693 | 0.34 | 18 |
| $Pr_2$CHNHC(O) | NHC$Me_2CMe_3$ | 693 | 0.51 | 38 |
| ($CH_2$=$CHCH_2$)$_2$—CHNHC(O) | NH—(R)—CH(Me)$CMe_3$ | 675 | 0.32 | 48 |
| $Pr_2$CHNHC(O) | NH—(R)—CH(Me)C(Me)$_2$—Et | 693 | 0.50 | 21 |
| $Pr_2$CHNHC(O) | cis-NH-(2-methyl-cyclohexyl) | 691 | 0.67 | 75 |
| $Pr_2$CHNHC(O) | trans-NH-(2-methyl-cyclohexyl) | 691 | 0.69 | 60 |
| (R,S)—EtPrCH—NHC(O) | NH$CH_2CMe_3$ | 651 | 0.23 | 35 |
| (R,S)—EtBUCH—NHC(O) | NH$CH_2CMe_3$ | 665 | 0.26 | 35 |
| $Pr_2$CHNHC(O) | NH—(R)—CH(Et)$CMe_3$ | 693 | 0.34 | 10 |
| $Pr_2$CHNHC(O) | NH-(2,2-dimethyl-cyclohexyl) | 706 | 0.40 | 24 |
| Et$Pr_2$CNHC(O) | NH—(R)—CH(Me)$CMe_3$ | 708 | 0.41 | 10 |
| $Pr_2$CHNHC(O) | NH$CH_2CMe_2$Pr | 694 | 0.42 | 35 |
| $Pr_2$CHNHC(O) | NH—(R)—CH(Me)—$CH_2CMe_3$ | 694 | 0.37 | 14 |

TABLE VI-continued

Compounds of Formula 1 having the formula A—B—Tbg—CH$_2$—(R)—CH—(CH$_2$C(O)CMe$_3$)C(O)—Asp(cyPn)—E wherein A—B and E are designated as follows:

| A—B | E | FAB/MS (m/z) (M+H)+ | IC$_{50}$ μM | EC$_{50}$ μM |
|---|---|---|---|---|
| Pr$_2$CHNHC(O) | NHCH$_2$CH$_2$CMe$_3$ | 701* | 0.58 | 72 |
| Pr$_2$CHNHC(O) | NH—(R)—CH(Pr)CMe$_3$ | 707 | 0.43 | 15 |
| Pr$_2$CHNHC(O) | NH-(2,2-dimethyl-cyclopentyl) | 691 | 0.38 | 31 |
| Pr$_2$CHNHC(O) | NH—N(Me)CMe$_3$ | 680 | 0.27 | 110 |
| Pr$_2$CHNHC(O) | NHCH$_2$CEt$_3$ | 707 | 0.52 | 19 |
| EtPr$_2$CNHC(O) | NH—(R)—CH(Et)CMe$_3$ | 722 | 0.36 | 6 |
| Pr$_2$CHNHC(O) | NH—(R)—CH(Me)CHEt$_2$ | 693 | 0.33 | 16 |
| Pr$_2$CHNHC(O) | NHN(Et)CMe$_3$ | 694 | 0.22 | 80 |

*(M + Na)

TABLE VII

| Compounds of Formula 1 | FAB/MS (m/z) (M + H)+ | IC$_{50}$ μM | EC$_{50}$ μM |
|---|---|---|---|
| Pr$_2$CHNHC(O)—Tbg—CH$_2$—(R)—CH(CH$_2$—C(O)CHMe$_2$)C(O)—Asp(cyPn)—NHCH$_2$—CMe$_3$ | 673* | 0.36 | 39 |
| Pr$_2$CHNHC(O)—Tbg—CH$_2$—(R)—CH—(CH$_2$C(O)CH$_2$CMe$_3$) C(O)—Asp(cyPn)—Leu—OH | 679 | 80 | |
| Pr$_2$CHNHC(O)—Tbg—CH$_2$—(R)—CH{CH$_2$—C(O)—(cyclohexyl)}C(O)—Asp(cyPn)—NHCH$_2$CMe$_3$ | 691 | 0.37 | 61 |
| Pr$_2$CHNHC(O)—Tbg—CH$_2$—(R)—CH{CH$_2$—C(O)—(cyclobutyl)}C(O)—Asp(cyPn)—NHCH$_2$CMe$_3$ | 663 | 0.31 | 46 |
| Pr$_2$CHNHC(O)—Tbg—CH$_2$—(R)—CH(CH$_2$—C(O)CMe$_3$)C(O)—Asp{(R)-allyl}-NHCH$_2$CMe$_3$ | 651 | 0.30 | 62 |
| Pr$_2$CHNHC(O)—Tbg—CH$_2$—(R)—CH(CH$_2$—C(O)CMe$_3$)C(O)—Asp{(R)—Pr}—NHCH$_2$CMe$_3$ | 653 | 0.25 | 46 |
| Pr$_2$CHNHC(O)—Tbg—CH$_2$—(R)—CH(CH$_2$—C(O)CMe$_2$Et)C(O)—Asp(cyPn)—NHCH$_2$—CMe$_3$ | 679 | 0.21 | 33 |
| Pr$_2$CHNHC(O)—Tbg—CH$_2$—(R)—CH{CH$_2$—C(O)—(1-methylcyclopentyl}C(O)—Asp(cyPn)—NHCH$_2$CMe$_3$ | 691 | 0.24 | 35 |
| Pr$_2$CHNHC(O)—NH—(S)—CH(CMe$_2$Et)—C(O)—CH$_2$—(R)—CH(CH$_2$C(O)CMe$_3$)C(O)—Asp—(cyPn)—NH—(R)—CH(Me)CMe$_3$ | 693 | 0.25 | 13 |
| Pr$_2$CHNHC(O)—Val—CH$_2$—(R)—CH(CH$_2$—C(O)CMe$_3$)C(O)—Asp(cyPn)—NH—(R)—CH(Me) CMe$_3$ | 665 | 0.22 | 37 |

*(M + Na)

We claim:

1. A compound of formula 1:
   A—B— Tbg—CH$_2$—(R)—CH(CH$_2$C(O)Me$_3$)C(O)—Asp(cyPn)-NH-R)-CH(Et)CMe$_3$ (1)

wherein
   A and B taken together form an alkylaminocarbonyl of the formula R$^5$—NH—C(O) wherein R$^5$ is a radical of formula Q:

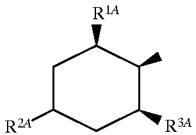

wherein R$^{1A}$ is (1–3C)alkyl, R$^{2A}$ is hydrogen or (1–3C)alkyl and R$^{A3}$ is (1-3C)alkyl; or a physiologically acceptable salt thereof.

2. The compound as recited in claim 1 wherein R$^{1A}$ and R$^{3A}$ are both methyl or both ethyl, and R$^{2A}$ is hydrogen, methyl or ethyl; or a physiologically acceptable salt thereof.

3. The compound as recited in claim 2 wherein R$^{1A}$ and R$^{3A}$ are both methyl and R$^{2a}$ is hydrogen or a cis-methyl relative to R$^{1A}$ and R$^{3A}$; or a physiologically acceptable salt thereof.

4. The compound as recited in claim 1 selected from the group consisting of {{(1α,2α,6α) -2,6-dimethyl-1-cyclohexanamino}carbonyl}—Tbg—CH$_2$—(R)—CH (CH$_2$—C(O)CMe$_3$)C(O)—Asp(cyPn)—NH—(R)—CH(Et) CMe$_3$, {{(1α,2α,6α)-2,6-diethyl-1-cyclohexanamino}-carbonyl}-Tbg-CH$_2$-(R)—CH(CH$_2$—C(O)CMe$_3$)C(O)-Asp (cyPn)-NH-(R)-CH(Et)CMe$_3$, and {{(1α,2α,4α,6α)-2,4,6-trimethyl-1-cyclohexanamino}carbonyl}-Tbg-CH$_2$-( R)-CH (CH$_2$-C(O)CMe$_3$)C(O)-Asp(cyPn)-NH-(R)-CH(Et)CMe$_3$.

5. A pharmaceutical composition comprising a compound as recited in claim 1 and a physiologically acceptable carrier.

6. A cosmetic composition comprising a compound as recited in claim 1 and a physiologically acceptable carrier suitable for topical application.

7. A method of treating a herpes viral infection in a mammal comprising administering to the mammal a therapeutically effective amount of a compound as recited in claim 1.

8. A method of inhibiting the replication of herpes virus by contacting the virus with a herpes viral ribonucleotide reductase inhibiting amount of a compound as recited in claim 1.

9. A pharmaceutical composition comprising an antiviral nucleoside analog, or a physiologically acceptable salt thereof, a compound as recited in claim 1 and a physiologically acceptable carrier.

10. The pharmaceutical composition of claim 9 wherein the antiviral nucleoside analog is a compound of formula 19:

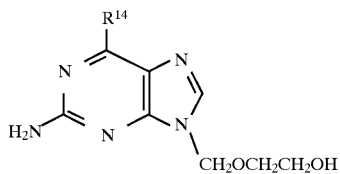

wherein R[14] in hydrogen, hydroxy or amino, or a therapeutically acceptable salt thereof.

11. A pharmaceutical composition of claim 9 wherein the antiviral nucleoside analog is selected from the group of penciclovir, famciclovir and valacyclovir.

12. A method of treating herpes viral infections in a mammal comprising administering thereto a therapeutically effective amount of pharmaceutical composition as recited in claim 9.

13. The method of claim 12 wherein the pharmaceutical composition is administered topically.

14. The method of claim 12 wherein the antiviral nucleoside analog in the pharmaceutical composition is selected from the group consisting of acyclovir, 6-deoxyacyclovir, 2,6-diamino-9-{(2-hydorxyethoxy)methyl}purine, penciclovir, famciclovir and valacyclovir.

15. A method of treating herpes simplex virus type 1, or type 2, infections in a mammal comprising administering thereto a therapeutically effective amount of a compound of claim 4.

16. A method of treating herpes viral infections in a mammal comprising administering thereto a therapeutically effective amount of an antiviral nucleoside analog, or a physiologically acceptable salt thereof, in conjunction with a compound as recited in claim 1, either sequentially or simultaneously.

* * * * *